United States Patent
Matsuyama et al.

(10) Patent No.: US 9,522,196 B2
(45) Date of Patent: Dec. 20, 2016

(54) ANTIBODY RECOGNIZING FOLATE RECEPTORS α AND β

(71) Applicant: KAGOSHIMA UNIVERSITY, Kagoshima (JP)

(72) Inventors: Takami Matsuyama, Kagoshima (JP); Taku Nagai, Kagoshima (JP); Kazuhisa Hasui, Kagoshima (JP); Sonshin Takao, Kagoshima (JP)

(73) Assignee: KAGOSHIMA UNIVERSITY, Kagoshima (JP)

( * ) Notice: Subject to any disclaimer, the term of this patent is extended or adjusted under 35 U.S.C. 154(b) by 0 days.

(21) Appl. No.: 14/654,951

(22) PCT Filed: Dec. 19, 2013

(86) PCT No.: PCT/JP2013/085026
§ 371 (c)(1),
(2) Date: Jun. 23, 2015

(87) PCT Pub. No.: WO2014/104270
PCT Pub. Date: Jul. 3, 2014

(65) Prior Publication Data
US 2015/0343088 A1 Dec. 3, 2015

(30) Foreign Application Priority Data
Dec. 25, 2012 (JP) ................................ 2012-281525

(51) Int. Cl.
| | | |
|---|---|---|
| *A61K 39/395* | (2006.01) | |
| *A61K 47/48* | (2006.01) | |
| *C07K 16/46* | (2006.01) | |
| *C07K 16/30* | (2006.01) | |
| *C07K 16/28* | (2006.01) | |
| *A61K 51/10* | (2006.01) | |
| *A61K 38/16* | (2006.01) | |
| *A61K 39/00* | (2006.01) | |

(52) U.S. Cl.
CPC ..... *A61K 47/48676* (2013.01); *A61K 51/1027* (2013.01); *C07K 16/28* (2013.01); *C07K 16/30* (2013.01); *C07K 16/468* (2013.01); *A61K 38/164* (2013.01); *A61K 2039/505* (2013.01); *C07K 2317/31* (2013.01); *C07K 2317/33* (2013.01); *C07K 2317/56* (2013.01); *C07K 2317/565* (2013.01); *C07K 2317/73* (2013.01); *C07K 2319/55* (2013.01)

(58) Field of Classification Search
None
See application file for complete search history.

(56) References Cited

U.S. PATENT DOCUMENTS

| 2008/0260812 A1 | 10/2008 | Matsuyama et al. |
| 2013/0230899 A1* | 9/2013 | Tei .......................... C07K 16/28 435/188 |
| 2014/0010756 A1 | 1/2014 | Takao et al. |

FOREIGN PATENT DOCUMENTS

| JP | 2010077026 A | 4/2010 |
| JP | 4805848 B2 | 11/2011 |
| JP | 4943144 B2 | 5/2012 |
| WO | 2005/080431 A2 | 9/2005 |
| WO | WO 2012/063955 * | 5/2012 |
| WO | 2012128377 A1 | 9/2012 |

OTHER PUBLICATIONS

Elnakat, et al., "Distribution, functionality and gene regulation of folate receptor isoforms: implications in targeted therapy", Advanced Drug Delivery Reviews, 2004, 56(8):1067-1084.
Jelovac, et al., "Role of farletuzumab in epithelial ovarian carcinoma", Current Pharmaceutical Design, 2012, 18 (25):3812-3815.
Nakashima-Matsushita, et al., "Selective expression of folate receptor beta and its possible role in methotrexate transport in synovial macrophages from patients with rheumatoid arthritis", Arthritis Rheumatism, 1999, 42 (8):1609-1616.
Nagai, et al., "Effect of an immunotoxin to folate receptor beta on bleomycin-induced experimental pulmonary fibrosis", Clinical and Experimental Immunology, 2010, 161(2):348-356.
Tsuneyoshi, et al., "Functional folate receptor beta-expressing macrophages in osteoarthritis synovium and their M1/M2 expression profiles", Scandinavian Journal of Rheumatology, 2012, 41(2):132-140.
Kurahara, et al., "Clinical significance of folate receptor B-expressing tumor-associated macrophages in pancreatic cancer", Annals Surgical Oncology, 2012, 19(7):2264-2271.
Nagai, et al., "Targeting tumor-associated macrophages in an experimental glioma model with a recombinant immunotoxin to folate receptor beta", Cancer Immunol Immunother, 2009, 58(10):1577-1586.
Ross, et al., "Folate Receptor Type beta Is a Neutrophilic Lineage Marker and Is Differentially Expressed in Myeloid Leukemia", Cancer, 1999, 85(2):348-357.
Coney, et al., "Cloning of a tumor-associated antigen: MOv18 and MOv19 antibodies recognize a folate-binding protein", Cancer Research, 1991, 51(22):6125-6132.
Ebel, et al., "Preclinical evaluation of MORAb-003, a humanized monoclonal antibody antagonizing folate receptor-alpha", Cancer Immunity, 2007, 7:p6, (2).

* cited by examiner

*Primary Examiner* — Marianne P Allen
(74) *Attorney, Agent, or Firm* — Lucas & Mercanti, LLP

(57) ABSTRACT

The object of the present invention is to provide an antibody capable of immunologically and specifically binding to a folate receptor α and a folate receptor β. Specifically, the present invention relates to an antibody or a fragment thereof, in which the amino acid sequences of CDRH1, CDRH2, and CDRH3 of a heavy chain variable region (VH) are SEQ ID NOs: 2, 4, and 6, respectively, and the amino acid sequences of CDRL1, CDRL2, and CDRL3 of a light chain variable region (VL) are SEQ ID NOs: 10, 12, and 14, respectively.

15 Claims, 9 Drawing Sheets
(2 of 9 Drawing Sheet(s) Filed in Color)

```
        <----------FWR1---------->
     Q V Q L K E S G P G L V Q P S Q T L S L T C T V S G F S L T
     CAGGTGCAGCTGAAGGAGTCAGGACCTGGTCTGGTGCAGCCTCACAGACCCTGTCCTCACTGCACTGTCTCTGGGTTCTCATTAACC
     <--CDR1--><         -----FWR2----->
     S N S V S  W  V R Q P P G K G L E W M G
     AGCAATAGTGTAAGC TGGGTTCGCCAGCCTCCGGAAAGGGTCTGGAGTGGATGGGA
     <-------CDR2------->
     A I W S G G S T D Y N S A L K S
     GCAATATGGAGTGGTGAAGCACAGATTATAATTCAGTCTCAAATCC
     <--------FWR3-------->
     R L S I S K D T S K S Q V F L K M N S L Q T E D T A I Y F C T R
     CGACTGAGCATCAGTAAGGACACCTCCAAGAGCCAAGTTTCTTAAAAATGAACAGTCTGCAAACTGAAGACACAGCCATTTACTTCTGTACCCGA
     <------CDR3------><--JK-->
     Y Y G Y T Y F A Y  W G Q G V M V T V S S
     TACTACGGGTATACCTACTTTGCTTAC TGGGGCCAAGGAGTCATGGTCACAGTCTCCTCA
```

(B)

```
        <----------FWR1---------->
     D I Q M T Q S P A S L S A S L E E I V T I T C Q A S Q D I G N W L A
     GACATCCAGATGACACAGTCTCCTGCCTCCCTGTCTGCATCTCTGGAAGAAATTGTCACCATCACATGCCAGGCAAGCCAAGACATTGGTAATTGGTTGGCA
     <------FWR2------>                   <--CDR2-->
     W Y Q Q K P G K S P Q L L I Y D A I R L A D
     TGGTATCAGCAGAAACCGGGGAAATCTCCTCAGCTCCTGATTTATGATGCAATCAGATTGGCAGAT
     <--------FWR3-------->
     G V P S R F S G S G S R S G T Q Y S L K I S R L Q V E D
     GGGGTCCCATCAAGGTTCAGCGGCAGTAGATCTGGCACAGTATTCCTTAAGATCAGCAGACTACACAGGTTGAAGAT
     <-----CDR3-----><---JK--->
     I G D Y Y C Q Q G S N P R T  F G G G T K L E L K
     ATTGGAGACTATTACTGTCAAAGGGTCAAAGTAATCCTCGGACG TTCGGTGGAGGCACCAAGCTGgaattgaaa
```

Fig. 2
(A) 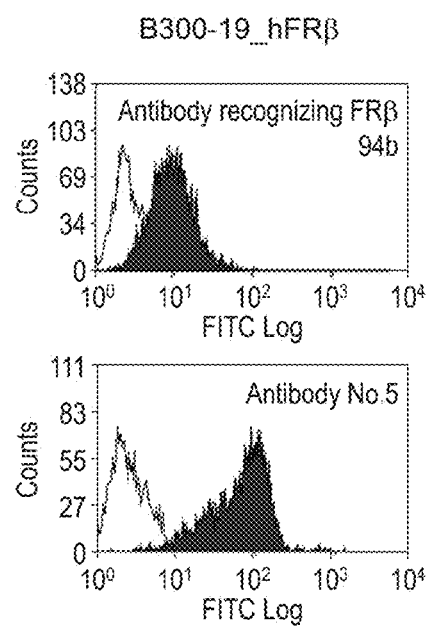
(B) 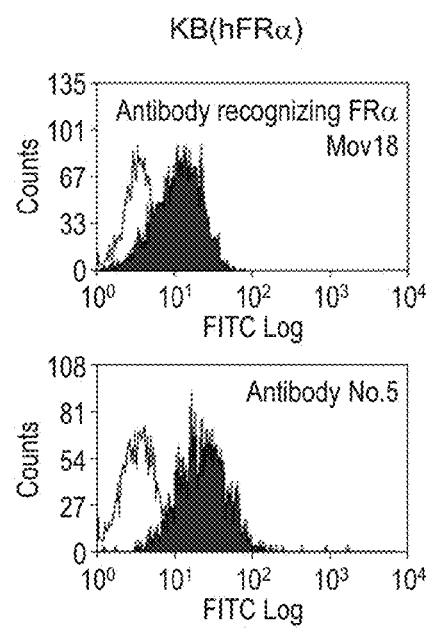

0.1 mm

Fig. 8
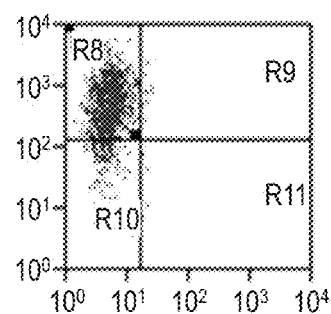
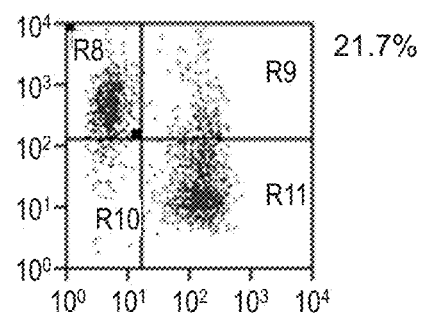
21.7%
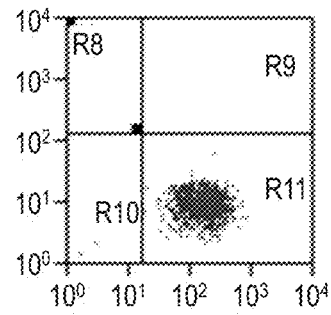
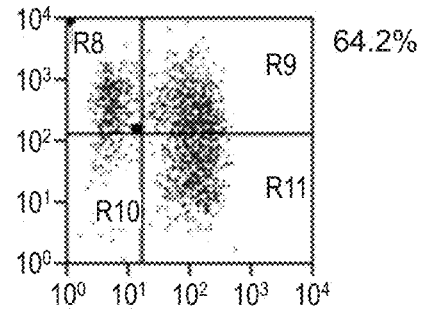
64.2%
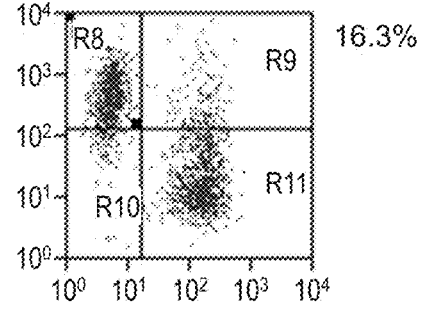
16.3%

ANTIBODY RECOGNIZING FOLATE RECEPTORS α AND β

CROSS-REFERENCE TO RELATED APPLICATIONS

This application is a 371 of PCT/JP2013/085026, filed Dec. 19, 2013, which claims the benefit of Japanese Patent Application No. 2012-281525, filed Dec. 25, 2012.

TECHNICAL FIELD

The present invention relates to an antibody recognizing folate receptors α and β and a cancer diagnostic agent and a cancer therapeutic agent comprising the antibody.

BACKGROUND ART

Folate receptors (FRs) are receptors of oxidized folate. It is known that folate receptor isoforms FRα, FRβ, and FRγ are present in human cells (Non-Patent Document 1).

FRα is expressed on epithelial cell surfaces, and the expression level of FRα increases in various cancer cells. Recently, a Phase II clinical study of an anti-FRα antibody for ovarian cancer patients was conducted in the U.S. and the effects of the antibody were confirmed (Non-Patent Document 2). In addition, Patent Document 1 discloses a therapeutic composition for ovarian cancer comprising an anti-FRα antibody.

FRβ is unlikely to be expressed in tissues of healthy individuals, and it tends to be expressed on activated macrophage surfaces in rheumatoid arthritis synovium, osteoarthritis synovium, inflammatory tissue such as lung tissue afflicted with pulmonary fibrosis, and the like (Non-Patent Documents 3-5). Further, the present inventors produced an anti-human FRβ antibody and revealed that most cancer-related macrophages present in various cancer tissues are FRβ-expressing macrophages, and cases of pancreatic cancer in which there is an increase in the number of FRβ-expressing macrophages is associated with poor prognosis (Non-Patent Document 6). The present inventors further revealed that removal of FRβ macrophages in a malignant glioma implantation model with the use of an anti-FRβ antibody immunotoxin results in inhibition of the growth of malignant glioma (Non-Patent Document 7). Moreover, Patent Documents 2-4 disclose an antibody against FR-β, an FR-β antibody immunotoxin obtained by binding the antibody and a toxin, and therapeutic agents comprising the antibody and the immunotoxin.

As stated above, it has been known that cancer growth inhibitory effects can be obtained through monotherapy with an anti-FRα antibody or a substance to which an anti-FRβ antibody is bound, such as an anti-FRβ antibody immunotoxin. However, there have been no reports indicating that cancer growth inhibitory effects can be obtained through a combination therapy of an anti-FRα antibody or a substance to which the antibody is bound and an anti-FRβ antibody or a substance to which the antibody is bound. In addition, although FRα and FRβ are about 70% identical to each other at the amino acid level, there have been no reports on an antibody recognizing both FRα and FRβ.

PRIOR ART DOCUMENTS

Patent Documents

Patent Document 1: JP Patent No. 4805848
Patent Document 2: JP Patent No. 4943144
Patent Document 3: JP Patent Publication (Kokai) No. 2010-77026 A
Patent Document 4: WO2012/128377

Non-Patent Documents

Non-Patent Document 1: Elnakat H., Ratnam M., Distribution, functionality and gene regulation of folate receptor isoforms: implications in targeted therapy, Adv Drug Deliv Rev., 2004 Apr. 29; 56(8): 1067-84
Non-Patent Document 2: Jelovac D., Armstrong D K., Role of farletuzumab in epithelial ovarian carcinoma, Curr Pharm Des., 2012; 18(25): 3812-5
Non-Patent Document 3: Nakashima-Matsushita N., Homma T., Yu S., Matsuda T., Sunahara N., Nakamura T., Tsukano M., Ratnam M., Matsuyama T., Selective expression of folate receptor beta and the possible role in methotrexate transport in synovial macrophages from patients with rheumatoid arthritis, Arthritis Rheum., 1999 August; 42(8): 1609-16
Non-Patent Document 4: Nagai T., Tanaka M., Hasui K., Shirahama H., Kitajima S., Yonezawa S., Xu B., Matsuyama T., Effect of an immunotoxin to folate receptor beta on bleomycin-induced experimental pulmonary fibrosis, Clin Exp Immunol., 2010 August; 161(2): 348-56
Non-Patent Document 5: Tsuneyoshi Y., Tanaka M., Nagai T., Sunahara N., Matsuda T., Sonoda T., Ijiri K., Komiya S., Matsuyama T., Functional folate receptor beta-expressing macrophages in osteoarthritis synovium and their M1/M2 expression profiles, Scand J Rheumatol., 2012; 41(2): 132-40
Non-Patent Document 6: Kurahara H., Takao S., Kuwahata T., Nagai T., Ding Q., Maeda K., Shinchi H., Mataki Y., Maemura K., Matsuyama T., Natsugoe S., Clinical significance of folate receptor β-expressing tumor-associated macrophages in pancreatic cancer, Ann Surg Oncol., 2012 July; 19(7): 2264-71
Non-Patent Document 7: Nagai T., Tanaka M., Tsuneyoshi Y., Xu B., Michie S A., Hasui K., Hirano H., Arita K., Matsuyama T., Targeting tumor-associated macrophages in an experimental glioma model with a recombinant immunotoxin to folate receptor beta, Cancer Immunol Immunother., 2009 October; 58(10): 1577-86

SUMMARY OF THE INVENTION

As stated above, there have been no reports indicating that cancer growth inhibitory effects can be obtained through a combination therapy of an anti-FRα antibody or a substance to which the antibody is bound and an anti-FRβ antibody or a substance to which the antibody is bound.

Hitherto, a variety of substances to which folate is bound have been suggested as diagnostic agents or therapeutic agents comprising FRα or FRβ (Muller C., Folate based radiopharmaceuticals for imaging and therapy of cancer and inflammation. Curr Pharm Des., 2012; 18(8): 1058-83; Clifton G T., Sears A K., Clive K S., Holmes J P., Mittendorf E A., Ioannides C G., Ponniah S., Peoples G E., Folate receptor α: a storied past and promising future in immunotherapy, Hum Vaccin., 2011 February; 7 (2): 183-90; and Low P S., Kularatne S A., Folate-targeted therapeutic and imaging agents for cancer. Curr Opin Chem Biol., 2009 Jun.; 13(3): 256-62). However, since folate is a low-molecular-weight substance, it is absorbed in a non-specific manner and it is also incorporated into cells by a proton-coupled folate transporter expressed in many cells in healthy tissue. Accordingly, it cannot be said that the effects of such substances to which folate is bound are specific to FRα-expressing cells or FRβ-expressing cells. In addition, intracellular absorption of a substance to which folate is bound is interfered with depending on the folate concentration in blood.

Meanwhile, compared with monotherapy with an anti-FRα antibody targeting cancer cells or an anti-FRβ antibody targeting cancer-related macrophages that promote cancer growth, cancer would be more effectively treated if an anti-FRα/β antibody specific to both FRα and FRβ and a compound of the antibody could be obtained and used for simultaneously damaging cancer cells and cancer-related macrophages. In addition, in the case of the conventional combined therapy involving two agents (i.e., an anti-FRα antibody and an anti-FRβ antibody), it would be more difficult to determine appropriate doses of the anti-FRα antibody and the anti-FRβ antibody because of the difference between the binding of the anti-FRα antibody to FRα-expressing cancer cells and the binding of the anti-FRβ antibody to FRβ-expressing macrophages, compared with the use of the anti-FRα/β antibody or a compound of the antibody. Further, the dose of the anti-FRα/β antibody can be reduced to a level lower than that in the combination therapy of the anti-FRα antibody and the anti-FRβ antibody. Thus, the anti-FRα/β antibody is economically advantageous.

In consideration of the above circumstances, the object of the present invention is to provide an antibody capable of specifically binding to both FRα and FRβ, which can be used for cancer diagnostic agents and cancer therapeutic agents.

As a result of intensive studies in order to achieve the object, the present inventors succeeded in producing an antibody capable of specifically binding to both FRα and FRβ. The present inventors found that the antibody reacts with cancer cells and cancer-related macrophages in various cancer tissues and also found that the antibody, in the presence of a complement, or an immunotoxin prepared with the antibody has cytotoxicity to both FRα-expressing cancer cells and FRβ-expressing cells.

This has led to the completion of the present invention.

Specifically, the present invention encompasses the following.

(1) An antibody capable of immunologically and specifically binding to FRα and FRβ.
(2) The antibody according to (1), wherein the antibody is selected from the group consisting of a monoclonal antibody, a polyclonal antibody, a chimeric antibody, a single chain antibody, a multispecific antibody, and fragments thereof.
(3) The antibody according to (1) or (2), which is a human antibody or a humanized antibody.
(4) The antibody according to any one of (1) to (3), which is an antibody or a fragment thereof, in which the amino acid sequences of CDRH1, CDRH2, and CDRH3 of a heavy chain variable region (VH) are the amino acid sequences of SEQ ID NOs: 2,4, and 6, respectively, and the amino acid sequences of CDRL1, CDRL2, and CDRL3 of a light chain variable region (VL) are the amino acid sequences of SEQ ID NOs: 10, 12, and 14, respectively.
(5) A molecular-targeted anticancer agent, which comprises the antibody according to any one of (1) to (4) or which is obtained by binding a drug to the antibody.
(6) The molecular-targeted anticancer agent according to (5), wherein the drug is selected from the group consisting of a toxin, a cytotoxic agent, an enzyme, a cytokine, and a chemotherapeutic agent.
(7) The molecular-targeted anticancer agent according to (6), wherein the toxin is a bacterium-derived toxin.
(8) The molecular-targeted anticancer agent according to (7), wherein the bacterium-derived toxin is *Pseudomonas* toxin, diphtheria toxin, or staphylococcal toxin.
(9) The molecular-targeted anticancer agent according to any one of (5) to (8), wherein the molecular-targeted anticancer agent is an immunotoxin.
(10) The molecular-targeted anticancer agent according to (6), wherein the cytotoxic agent is selected from the group consisting of an antitumor agent, a tumor growth inhibitor, a tumor cell apoptosis inducer, and a radioactive nuclide.
(11) A pharmaceutical composition for cancer treatment, which comprises the molecular-targeted anticancer agent according to any one of (5) to (10) and a pharmaceutically acceptable carrier.
(12) A cancer diagnostic agent, which is obtained by binding a label to the antibody according to any one of (1) to (4).
(13) The cancer diagnostic agent according to (12), wherein the label is a fluorophore, a pigment, or a radioactive isotope.
(14) A cancer diagnostic kit, which comprises the antibody according to any one of claims 1 to 4 or the cancer diagnostic agent according to (12) or (13).

This description includes all or part of the contents as disclosed in the description and/or drawings of Japanese Patent Application No. 2012-281525, which is a priority document of the present application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the nucleotide sequence (SEQ ID NO: 7) and the amino acid sequence (SEQ ID NO: 8) of the heavy chain region of the anti-human FRα/β rat monoclonal antibody (A) and the nucleotide sequence (SEQ ID NO: 15) and the amino acid sequence (SEQ ID NO: 16) of the light chain region of the anti-human FRα/β rat monoclonal antibody (B).

FIG. 2 shows flow cytometry results indicating reactivity of the anti-human FRα/β rat monoclonal antibody to human FRβ-expressing cells (A) and human FRα-expressing cells (B).

FIG. 8 (A)-(E) show flow cytometry results indicating the effects of the anti-human FRα/β rat monoclonal antibody to enhance the capacity of macrophages to phagocytize folate receptor α-expressing cancer cells.

MODE FOR CARRYING OUT THE INVENTION

Figure 3:
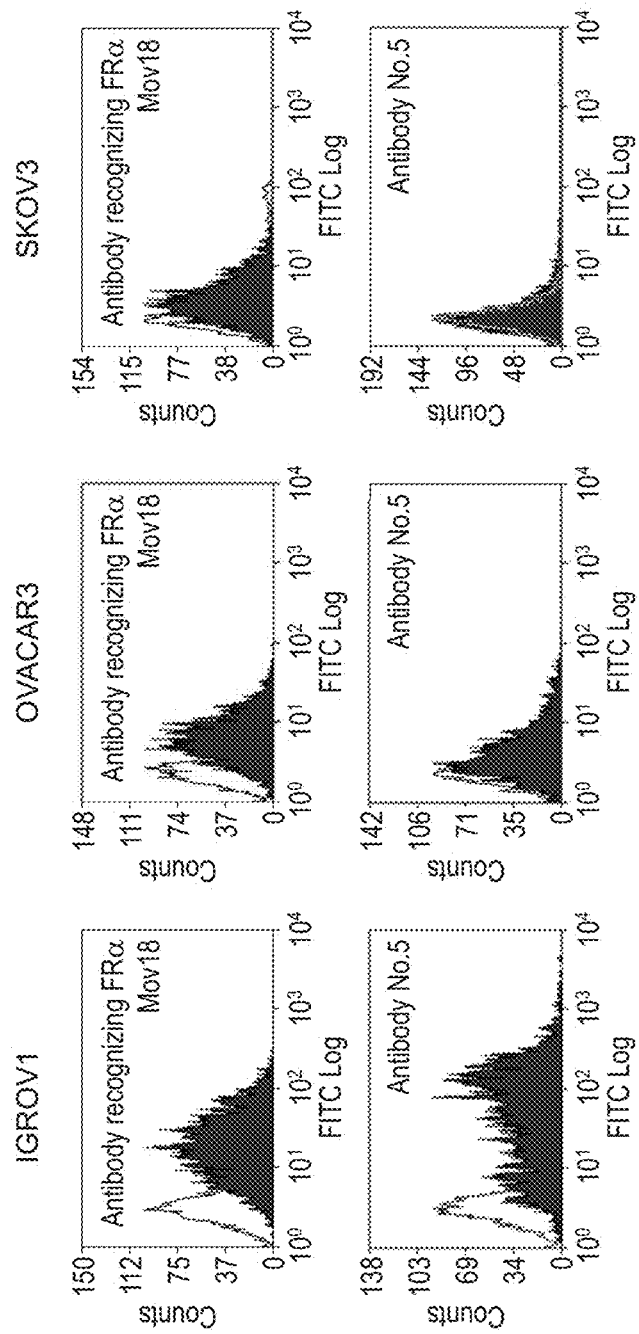
FIG. 3 shows flow cytometry results indicating reactivity of the anti-human FRα/β rat monoclonal antibody to human ovarian cancer cell lines.

The present invention will be described in more detail.
<Definition>

The term "folate receptor α" or "FRα" as used herein refers to a receptor protein expressed on a cancer cell surface in a subject.

The term "folate receptor β" or "FRβ" as used herein refers to a receptor protein expressed on a cancer-related macrophage cell surface in a subject.

The term "subject" as used herein refers to, for example, mammalian animals, such as primates including humans, livestock animals such as cattle, pigs, horses, goats, and sheep, and pet animals such as dogs and cats. A preferable subject is a human.

As used herein, the term "an antibody binding immunologically and specifically to FRα and FRβ" or "an anti-FRα/β antibody" refers to an antibody which does not bind to proteins other than the FRα protein and the FRβ protein or naturally-occurring variants thereof or does not substantially bind to other proteins.
<Anti-FRα/β Antibody>

The term "anti-FRα/β antibody" as used herein refers to an antibody, or a fragment thereof, that is capable of recognizing and binding to both the FRα protein and the FRβ protein, regardless of a type or form of an antibody, as described below. Such antibodies enable specific binding to both the cell surface FRα protein on a cancer cell and the cell surface FRβ protein on a cancer-related macrophage that promotes cancer growth.

In the present invention, the above antibody binds to FRα and FRβ via immunological reaction; however, such antibody does not substantially bind to proteins other than FRα and FRβ or variant proteins thereof having 90% or higher, preferably 95% or higher, and more preferably 98% or higher sequence identity with FRα and FRβ.

The anti-FRα/β antibody according to the present invention may be of any immunoglobulin (Ig) class (e.g., IgA, IgG, IgE, IgD, IgM, or IgY) and any subclass (e.g., IgG1, IgG2, IgG3, IgG4, IgA1, or IgA2). Also, an immunoglobulin light chain may be the κ or λ chain.

Specifically, the anti-FRα/β antibody according to the present invention is, for example, an antibody having a complete structure of the aforementioned class or subclass, or a fragment of the antibody, such as a recombinant antibody, a single chain antibody (scFv), a multispecific antibody (e.g., a double-specific antibody, a diabody, a triabody, ScDb (single chain diabody), and dsFv-dsFv), a chimeric antibody, a humanized antibody, or a human antibody, or a fragment of any thereof.

An antibody fragment that can be used in the present invention is capable of binding to an epitope of the FRα protein antigen and an epitope of the FRβ protein antigen comprising 7 or more, and preferably at least 8 to 12 continuous amino acids.

Examples of antibody fragments include Fab, Fab', F(ab')$_2$, Fv, Fd, and Fabc. Antibody fragments can be prepared by methods known in the art. For example, antibody fragments can be prepared by digesting antibody molecules with a protease such as papain or pepsin or by known genetic engineering techniques.

Hereafter, methods for preparing antibodies used in the present invention are described in detail.

In order to prepare antibodies that can be used in the present invention, at the outset, the FRα protein and the FRβ protein to be used as an immunogen (i.e., an antigen) or fragments of the proteins are prepared.

A fragment comprises an amino acid sequence comprising 7-10 or more, such as 11-25, continuous amino acids. The origins of the FRα protein and the FRβ protein that can be used as an immunogen are not particularly limited, provided that they are capable of inducing an antibody that can bind specifically to target FRα and FRβ.

In order to induce an antibody that can bind specifically to FRα and FRβ, FRα (which has an approximately 70% sequence identity with FRβ at the amino acid level) is aligned with FRβ, and a (poly)peptide comprising a partial sequence having a high identity between the sequence portions comprising approximately 7-20 continuous amino acids can be selected as the immunogen. In such a case, it is preferable that an FRα protein surface structure and an FRβ protein surface structure are predicted with the utilization of, for example, the results of hydrophilicity/hydrophobicity prediction using the Kyte-Doolittle method or secondary structure prediction based on amino acid sequences by the Chou-Fasman method (Biochemistry 1974, 13: 222-244) to select the (poly)peptide sequence exposed on the surfaces of the proteins as the immunogen.

The information concerning the amino acid sequences or nucleotide sequences of the FRα protein and the FRβ protein of mammalian animals, including humans, of the FRα protein and the FRβ protein or fragments thereof used for preparing the antibody of the present invention is available from GenBank (NCBI, U.S.A.), EMBL (EBI, Europe), or the like. The accession numbers of the amino acid sequence and the nucleotide sequence of human FRα registered at the GenBank include NM_016725 (transcript variant 1), NM_00802 (transcript variant 2), and NM_016729 (transcript variant 4). The accession numbers of the amino acid sequence and the nucleotide sequence of human FRβ registered at the GenBank include some known variants, and examples thereof include NM_000803 (transcript variant 1), NM_001113534 (transcript variant 2), and NM_001113535 (transcript variant 3). The FRα protein and the FRβ protein or fragments thereof can be produced via peptide synthesis or genetic recombination techniques known in the art based on the sequence information above.

FRα and FRβ variants or orthologs of the same or different animal species can be searched with the use of the algorithm described by, for example, Karlin and Altschul (1993, Proc. Natl. Acad. Sci., U.S.A., 90: 5873-5877) or the modified algorithm (Karlin and Altschul, 1990, Proc. Natl. Acad. Sci., U.S.A., 87: 2264). Such algorithm is incorporated into the NBLAST and XBLAST programs described in Altschul et al. (1990, J. Mol. Biol., 215: 403). In addition, Gapped BLAST described by Altschul et al. (1997, Nucleic Acids Res. 25: 3389) can be employed in order to obtain a gap-introduced alignment.

Peptide synthesis can be carried out by a liquid-phase method or a solid-phase method. While a difference between such techniques lies only in the use of a solid-phase, the solid-phase method is more advantageous in terms of easy collection of products. Thus, the solid-phase method is effectively employed. Both methods each comprise synthesizing large number of peptides comprising approximately 5 to 10 (protective) amino acids constituting a protein, extending the peptides in a stepwise manner to synthesize polypeptides, and removing the protective groups in the end to produce a target protein, followed by purification. The method of peptide synthesis is described in, for example, *Seikagaku Jikken Kouza* 1 (Lecture Course for Biochemical Experiment) vol. 1, *Tanpakushitsu no Kagaku* (Protein Chemistry) IV, Kagaku shushoku to Peptide Gousei (Chemical Modification and Peptide Synthesis), the Japanese Biochemical Society (ed.), Tokyo Kagaku Dojin Co. Ltd.

According to genetic engineering techniques, for example, DNA encoding the FRα protein or FRβ protein is ligated to an adequate vector, the resulting vector is introduced into an adequate host cell for transformation, and the host cell is cultured in an adequate medium to produce the FRα protein or FRβ protein. These techniques are well-known to a person skilled in the art, and vectors, host cells, and transformation, culture, protein purification, and other techniques are described in, for example, Sambrook et al., Molecular Cloning: A Laboratory Manual, vol. 2, Cold Spring Harbor Laboratory Press, 1989; and Ausubel et al., Current Protocols in Molecular Biology, John Wiley & Sons, 1998.

Examples of antibody-producing cells include: insect cells such as *Spodoptera frugiperda* cells; yeast cells such as *Saccharomyces cerevisiae* and *Schizosaccharomyces pombe*; and mammalian cells such as Chinese hamster ovary (CHO) cells, hamster embryonic kidney cells, human embryonic kidney 293 cells, normal dog kidney cells, normal cat kidney cells, monkey kidney cells, African green monkey kidney cells, COS cells, non-tumor mouse muscle myoblasts (G8), fibroblasts, myeloma cells, mouse NIH/3T3 cells, LMTK cells, mouse sertoli cells, human cervical cancer cells, buffalo rat liver cells, human lung cells, human liver cells, mouse breast cancer cells, TRI cells, MRC5 cells, and FS4 cells.

Non-human animals are immunized with the thus-produced FRα and FRβ proteins or fragments thereof as the immunogen, and the antibody according to the present invention can be produced by the method described below. It is also possible to prepare either the FRα protein or the FRβ protein or a fragment thereof as the immunogen and examine whether the obtained antibodies bind to the protein that is the origin of the immunogen as well as to the other protein so as to determine an antibody capable of binding to both the FRα protein and the FRβ protein to be the anti-FRα/β antibody of the present invention. Alternatively, DNA encoding the heavy chain and light chain variable regions encoding such antibody is prepared from mRNA of the spleen cells, lymph cells, or other cells of the immunized non-human animals, and the resulting DNA can be used to synthesize DNA encoding synthetic antibodies of various forms, such as chimeric antibodies.

Examples of antibodies that can be used in the present invention include, but are not limited to, polyclonal antibodies, monoclonal antibodies, recombinant antibodies (e.g., chimeric antibodies, single chain antibodies, multispecific antibodies, and humanized antibodies), and human antibodies.

Polyclonal antibodies can be produced by immunizing mammalian animals, such as rabbits, rats, or mice, with the immunogen prepared in the manner described above and obtaining the antiserum. Specifically, the immunogen is intravenously, subcutaneously, or intraperitoneally administered to mammalian animals together with an adjuvant to enhance the immunogenicity, according to need. Examples of adjuvant that can be used include commercially available complete Freund's adjuvants, incomplete Freund's adjuvants, aluminum salts (Alum) such as aluminum hydroxide, and muramyl peptide (i.e., a type of peptide associated with a bacterial cell wall). Thereafter, immunization is performed 1 to 7 times at intervals of several days to several weeks, the antibody titer is assayed 1 to 7 days after the final immunization via enzyme immunoassay techniques, such as ELISA, and the blood is sampled when the maximal antibody titer is measured, so as to obtain the antiserum. The thus-obtained antiserum may be used as such. Alternatively, the antiserum may be purified before use by applying the antiserum to an affinity column on which the FRα protein and the FRβ protein or fragment peptides thereof have been immobilized (e.g., an agarose gel column) and then recovering antibodies bound to the column.

Monoclonal antibodies can be prepared in the manner described below. Specifically, hybridomas are prepared from the antibody-producing cells obtained from non-human mammalian animals that were immunized in the manner described above (e.g., spleen cells or lymphoid cells) and immortalized myeloma cells by the fusion technique, the hybridomas are subjected to cloning, and clones producing monoclonal antibodies showing specific affinity to the FRα protein and the FRβ protein or fragment peptide antigens thereof used for immunization are selected using a medium containing hypoxanthine, aminopterin, and thymidine (i.e., HAT medium). Thus, monoclonal antibodies can be prepared. Hybridomas can be prepared in accordance with, for example, the method of Kohler and Milstein et al. (Nature, 1975, 256: 495-96). Examples of non-human mammalian animals include rodents such as mice and rats. As myeloma cells, cells originating from the animals of the same species with the immunized animals are preferably used, and examples thereof include mouse myeloma cells and rat myeloma cells. Specific examples of mouse myeloma cell lines include P3-NS1/1-Ag4-1, P3-x63-Ag8.653, and Sp2/O-Ag14 cell lines. Antibody-producing cells can be fused to myeloma cells with the use of polyethylene glycol (PEG) having the average molecular weight of about 1,500 or via electroporation.

Chimeric antibodies, recombinant antibodies, single chain antibodies, humanized antibodies, and the like can be produced from DNAs encoding the antibodies derived from hybridomas producing specific monoclonal antibodies prepared from the spleen cells and the myeloma cells from non-human animals that were immunized with the FRα protein and the FRβ protein or fragment peptides thereof.

Specifically, total RNA is extracted from the hybridoma cells, mRNAs showing binding affinity for the oligo dT column are recovered from total RNA, cDNA is synthesized, and DNA encoding a particular monoclonal antibody is cloned. Alternatively, DNA encoding an antibody of interest is synthesized via PCR amplification based on the known immunoglobulin gene sequence, and the DNA sequence is determined. The sequences and the positions of the variable regions, complementarity-determining regions (CDRs), and framework regions (FRs) of the antibody heavy (H) chain and light (L) chain of animals, such as humans or mice, can be determined in accordance with, for example, the Kabat's EU numbering index (Kabat E. A. et al., Sequences of Proteins of Immunological Interest, 5th ed., Vol. 1, Bethesda (Md.): NIH, 1991).

Methods for preparing recombinant antibodies using genetic engineering techniques are described in greater detail.

Genes encoding monoclonal antibodies are cloned from the prepared hybridomas and integrated into adequate vectors, the resultants are introduced into host cells, such as mammalian cells such as Chinese hamster ovary (CHO) cells, E. coli cells, yeast cells, insect cells, or plant cells, and recombinant antibodies can be produced in the host cells (P. J. Delves., ANTIBODY PRODUCTION ESSENTIAL TECHNIQUES., 1997, WILEY, P. Shepherd and C. Dean., Monoclonal Antibodies., 2000, OXFORD UNIVERSITY PRESS, J. W. Goding., Monoclonal Antibodies: Principles and Practice, 1993 ACADEMIC PRESS). Alternatively, transgenic mice, cattle, goats, sheep, or pigs in which the endogenous gene locus has been substituted with the gene locus of a target antibody are prepared by techniques for producing transgenic animals, the resulting transgenic animals are immunized with the FRα protein and the FRβ protein or fragment peptides thereof as the immunogen, and the antibodies derived from the antibody gene can be obtained from, for example, the blood or milk of such transgenic animals. Some of the above-mentioned transgenic animals are human antibody producing animals such as mice or cattle that lack endogenous antibody genes and possess the human antibody genes. When utilizing such animals, accordingly, complete human antibodies binding to human FRα and FRβ can be obtained (e.g., WO 96/34096, WO 96/33735, and WO 98/24893). When hybridomas prepared from the antibody-producing cells of the animals (e.g., B cells) and myeloma cells are cultured in vitro, further, monoclonal antibodies can be produced in the manner described above.

The monoclonal antibodies prepared can be purified by methods known in the art, such as chromatography involving the use of a protein A or G column, ion exchange chromatography, hydrophobic chromatography, salting out with ammonium sulfate, gel filtration, or affinity chromatography, and such techniques can be performed in adequate combination.

Chimeric antibodies comprise H-chain and L-chain variable regions and constant regions originating from different animal species. For example, chimeric antibodies comprise H-chain and L-chain variable regions originating from mouse or rat antibodies and H-chain and L-chain constant regions originating from human antibodies. DNA encoding such antibodies comprises a nucleotide sequence resulting from substitution of a DNA sequence encoding a constant region in the DNA sequence encoding mouse or rat antibodies with a DNA sequence encoding a human constant region. Chimeric antibodies can be produced by the technique described in, for example, Morrison et al., 1984, Proc. Natl. Acad. Sci., 81: 6851-6855; Neuberger et al., 1984, Nature, 312: 604-608; Takeda et al., 1985, Nature, 314: 452-454.

Humanized antibodies comprise H-chain and L-chain CDRs originating from non-human animals and constant regions and framework regions originating from humans. For example, humanized antibodies comprise H-chain and L-chain CDRs (CDR1, CDR2, and CDR3) originating from mouse or rat antibodies and constant (C) regions and framework regions (FR1, FR2, FR3, and FR4) originating from human antibodies. DNA encoding such antibodies comprises a nucleotide sequence resulting from substitution of DNA sequences encoding the constant regions and the framework regions of the DNA sequence encoding mouse or rat antibodies with DNA sequences encoding the constant regions and the framework regions originating from human antibodies. A technique for preparing humanized antibodies is a so-called CDR grafting technique. Among the antibodies used in the present invention, in particular, antibodies that can be administered to humans can be prepared by the CDR grafting technique (Jones et al., Nature, 321: 522-525, 1986; Reichmann et al., Nature, 332: 323-329, 1988; Presta, Curr. Op. Struct. Biol., 2: 593-596, 1992; Verhoeyen et al., Science, 239: 1534-1536, 1988). Alternatively, complete human antibodies can be produced with the use of non-human animals that produce human antibodies (e.g., mice) or by the phage display technique, as described below.

According to the phage display technique, phages such as filamentous bacteriophages M13 or bacteriophages T7 are used to express fusion proteins of phage coat proteins with foreign polypeptides (e.g., recombinant anti-FRα/β antibodies) and present the fusion proteins on the phage surface (e.g., C. Barbas et al., Phage Display: Laboratory Manual, Cold Spring Harbor Laboratory Press, 2001). As phage coat proteins, g3p or g8p in the M13 phage or g10p in the T7 phage can be used to present foreign polypeptides. Examples of recombinant anti-FRα/β antibodies include single chain antibodies (scFv) comprising the H chain variable region (VH) bound to the L-chain variable region (VL) through a linker (e.g., $(GGGGS)_3$), synthetic antibodies such as multispecific antibodies (i.e., antibodies comprising two or more different VHs in combination with two or more different VLs), and (recombinant) H-chain (VH and CH) or L-chain (VL and CL) of (human) antibodies, or a combination thereof.

Specific examples of the antibodies that can be used in the present invention and produced by the method described above include, but are not limited to, the antibodies described below. In addition to the antibodies described below, recombinant antibodies such as chimeric antibodies, single chain antibodies, or multispecific antibodies comprising the complementarity determining regions of the heavy chain variable region and the light chain variable region of the antibodies can be contained as active ingredients into the composition, kit, and diagnostic agent of the present invention.

The following antibodies prepared in the Examples below are shown in FIG. 1:

an antibody or a fragment thereof, comprising the heavy chain variable region (VH) of the amino acid sequence as shown in SEQ ID NO: 8 (the corresponding nucleotide sequence: SEQ ID NO: 7) and the light chain variable region (VL) of the amino acid sequence as shown in SEQ ID NO: 16 (the corresponding nucleotide sequence: SEQ ID NO: 15), derived from the anti-human FRα/β rat monoclonal antibody (clone name: No. 5); and an antibody or a fragment thereof, comprising the heavy chain variable region (VH) comprising CDRH1, CDRH2, and CDRH3 of the amino acid sequences as shown in SEQ ID NOs: 2, 4, and 6, respectively, and the light chain variable region (VL) comprising CDRL1, CDRL2, and CDRL3 of the amino acid sequences as shown in SEQ ID NOs: 10, 12, and 14, respectively, derived from the anti-human FRα/β rat monoclonal antibody (clone name: No. 5).

The above antibodies can comprise mutation, such as substitution, deletion, or addition (or insertion) of 1 to 3, and preferably 1 or 2 amino acid residues, in the heavy chain variable region, the light chain variable region, the framework region, or the constant region. A specific example thereof is provided below:

an antibody or a fragment thereof, comprising the amino acid sequence as shown in SEQ ID NO: 18 (the corresponding nucleotide sequence: SEQ ID NO: 17) having a substitution of glycine (amino acid 44) with cysteine in the amino acid sequence as shown in SEQ ID NO: 8 (the corresponding nucleotide sequence: SEQ ID NO: 7) of the heavy chain variable region (VH) and the amino acid sequence as shown in SEQ ID NO: 20 (the corresponding nucleotide sequence: SEQ ID NO: 19) having a substitution of glycine (amino acid 100) with cysteine in the amino acid sequence as shown in SEQ ID NO: 16 (the corresponding nucleotide sequence: SEQ ID NO: 15) of the light chain variable region (VL), derived from the anti-human FRα/β rat monoclonal antibody (clone name: No. 5).

A humanized antibody comprises the sequences of the heavy chain CDR1 to CDR3 and the light chain CDR1 to CDR3 of the above antibody and the sequences of the heavy chain framework region and constant region and the light chain framework region and constant region, derived from a human, for example. The amino acid sequences of the framework region and the constant region can comprise mutation, such as substitution, deletion, or addition (or insertion) of 1 to 3, and preferably 1 or 2 amino acid residues, without changing the binding specificity for the FRα protein and the FRβ protein. A specific example of humanized antibodies is provided below:

a humanized antibody or a fragment thereof, comprising the heavy chain variable region (VH) comprising CDRH1, CDRH2, and CDRH3 of the amino acid sequences as shown in SEQ ID NOs: 2, 4, and 6, respectively, and the light chain variable region (VL) comprising CDRL1, CDRL2, and CDRL3 of the amino acid sequences as shown in SEQ ID NOs: 10, 12, and 14, respectively.

As described in the examples below, after mutant VH and mutant VL were prepared by introducing Cys substitution into VH or VL of the anti-human FRα/β rat monoclonal antibody (clone name: No. 5), a toxin polypeptide (e.g., *Pseudomonas* Exotoxin (PE)) is allowed to fuse to each mutant VH to prepare an immunotoxin VH, to which each mutant VL is subsequently allowed to bind, thereby producing an immunotoxin.

The antibodies of the present invention bind immunologically and specifically to the FRα protein and the FRβ protein, and the dissociation constant ($K_d$) is, for example, $1 \times 10^{-7}$ M or less, $1 \times 10^{-8}$ M or less, $1 \times 10^{-9}$ M or less, $1 \times 10^{-10}$ M or less, $1 \times 10^{-11}$ M or less, $1 \times 10^{-12}$ M or less, $1 \times 10^{-13}$ M or less, $1 \times 10^{-14}$ M or less, or $1 \times 10^{-15}$ M or less.

<Molecular-Targeted Anticancer Agent>

According to the present invention, a molecular-targeted anticancer agent comprising the antibodies and a drug bound thereto is used as a therapeutic agent for cancer or an active ingredient of a therapeutic agent for cancer or for the production of such therapeutic agent.

In another aspect of the present invention, since the above antibodies have cytotoxicity (complement-dependent cytotoxicity) to FRα-expressing cancer cells and FRβ-expressing cells in the presence of a complement, or promote the capacity of macrophages to phagocytize FRα-expressing cancer cells (ADCP: antibody-dependent cell mediated phagocytosis), a molecular-targeted anticancer agent comprising or consisting of the above antibodies can be used as a therapeutic agent for cancer or an active ingredient of a therapeutic agent for cancer or for the production of such therapeutic agent.

FRα is expressed on cancer cells of various cancers (e.g., ovarian cancer, breast cancer, malignant mesothelioma, lung cancer, large bowel cancer, malignant melanoma, glioblastoma, kidney cancer, and pancreatic cancer), and FRβ is expressed on cancer-related macrophages that promote cancer growth (Non-Patent Documents 6 and 7; Davidson B., The diagnostic and molecular characteristics of malignant mesothelioma and ovarian/peritoneal serous carcinoma. Cytopathology, 2011 February; 22 (1): 5-21. doi: 10.1111/j.1365-2303; Parker N., Turk M J., Westrick E., Lewis J D., Low P S., Leamon C P., Folate receptor expression in carcinomas and normal tissues determined by a quantitative radioligand binding assay. Anal Biochem., 2005 Mar. 15; 338 (2): 284-93; Sanchez-del-Campo L., Montenegro M F., Cabezas-Herrera J., Rodriguez-Lopez J N., The critical role of alpha-folate receptor in the resistance of melanoma to methotrexate. Dye Cell Melanoma Res., 2009 October; 22 (5): 588-600; Puig-Kroger A., Sierra-Filardi E., Dominguez-Soto A., Samaniego R., Corcuera M T., Gomez-Aguado F., Ratnam M., Sanchez-Mateos P., Corbi A L., Folate receptor beta is expressed by tumor-associated macrophages and constitutes a marker for M2 anti-inflammatory/regulatory macrophages. Cancer Res. 2009 Dec. 15; 69 (24): 9395-403). In addition, an example of a cancer-related macrophage is an FRβ-expressing macrophage that exists around pancreatic cancer cells at the invasive front (Patent Document 4).

Therefore, in the case of the molecular-targeted anticancer agent comprising the anti-FRα/β antibody and a drug bound thereto, the anti-FRα/β antibody binds to FRα-expressing cancer cells and FRβ-expressing cancer-related macrophages such that a drug contained in the molecular-targeted anticancer agent inhibits the growth of FRα-expressing cancer cells and the growth of FRβ-expressing cancer-related macrophages, thereby making it possible to treat cancer. Alternatively, the molecular-targeted anticancer agent comprising or consisting of the anti-FRα/β antibody binds to FRα-expressing cancer cells and FRβ-expressing cancer-related macrophages such that the growth of FRα-expressing cancer cells and the growth of FRβ-expressing cancer-related macrophages are inhibited due to complement-dependent cytotoxicity, thereby making it possible to treat cancer.

Cancers to be treated with the molecular-targeted anticancer agent are not particularly limited as long as the relevant cancer cells express FRα and cancer-related macrophages express FRβ. Examples thereof include ovarian cancer, breast cancer, malignant mesothelioma, lung cancer, large bowel cancer, malignant melanoma, glioblastoma, kidney cancer, pancreatic cancer, and oral cavity cancer (oral epidermoid cancer).

Drugs that are bound to the anti-FRα/β antibody are not particularly limited. However, examples thereof include toxins, cytotoxic agents, enzymes, cytokines, and chemotherapeutic agents.

Examples of toxins include, but are not limited to, bacterial toxins, phytotoxins, endotoxins, and exotoxins. Specific examples include bacterial toxins, such as diphteria toxin, *Pseudomonas* toxin, ricin A chain or deglycosylated ricin A chain of *Pseudomonas aeruginosa* exotoxin, *Pseudomonas* exotoxin PE38, ribosome inactivating protein, abrin A chain, modeccin A chain, alpha-sarcin, gelonin, aspergillin, restrictocin, ribonuclease, epidophyllotoxin, diphtheria toxin, diphtheria A chain, and staphylococcal toxin (e.g., staphylococcal enterotoxin).

Examples of cytotoxic agents against tumor cells include antitumor agents, tumor growth inhibitors, cell cycle arrest inducers, DNA synthesis inhibitors, transcription inhibitors, translation/protein synthesis inhibitors, cell division inhibitors, microtubule inhibitors, a variety of signal transduction inhibitors, microRNA, SiRNA, inducers of apoptosis against tumor cells, and radioactive nuclides.

Examples of cytotoxic agents include, but are not limited to, pokeweed anti-viral protein, abrin, ricin and ricin A chain, altretamine, actinomycin D, plicamycin, puromycin, gramicidin D, doxorubicin, colchicine, cytochalasin B, cyclophosphamide, emetine, maytansine, amsacrine, cisplatin, etoposide, etoposide ortho-quinone, teniposide, daunorubicin, gemcitabine, doxorubicin, mitoxantraone, bisantrene, bleomycin, methotrexate, vindesine, vinorelbine, podophyllotoxin, adriamycin, vincristine, vinblastine, BCNU, Taxol, Tarceva, Avastin, mitomycin, modified *Pseudomonous* enterotoxin A, calicheamicin, 5-fluorouracil, and cyclophosphamide.

Examples of radioactive nuclides include, but are not limited to, radioactive isotopes, such as lead-212, bismuth-212, astatine-211, iodine-131, scandium-47, rhenium-186, rhenium-188, samarium-153, yttrium-90, iodine-123, iodine-125, iodine-131, bromine-77, indium-111, phosphorus-32, and boron-10, or fissionable nuclides such as actinides. Labeling can be performed via an amino acid residue in a protein, such as a cysteine or lysine residue. Labeling techniques are described in, for example, Monoclonal Antibodies in Immunoscintigraphy (Chatal, CRC Press, 1989).

Examples of enzymes include ribonuclease and caspase.
Examples of cytokines include IL-2 and TNF-α.
Examples of chemotherapeutic agents include maytansinoid, auristatin, and pemetrexed.

When the molecular-targeted anticancer agent of the present invention comprises the antibody and the toxin (i.e., an immunotoxin), such ingredients can be in the form of a fusion protein. In such a case, a toxin can bind to, for example, the framework region or the C-terminal region in the variable region or the CH3 region or the C-terminal region in the constant region of the antibody protein through a linker (e.g., a peptide), according to need. When the molecular-targeted anticancer agent of the present invention comprises the antibody and the toxin or the cytotoxic agent, however, such ingredients can bind to each other via a covalent or non-covalent bond through functional groups. For example, a reactive group in an antibody molecule, such as a functional group such as an amino, carboxyl, hydroxyl, or mercapto group, is allowed to react with a toxin or cytotoxic agent having a reactive group, so as to produce a molecular-targeted agent. Examples of the reactive group include N-succinimidyl ester, N-sulfosuccinimidyl ester, carboxyl, amino, mercapto, and disulfide groups. Binding can be performed with the use of a coupling agent, such as a bifunctional coupling agent, active ester, aldehydes, bisazide, or isocyanate.

Further, the molecular-targeted anticancer agent of the present invention can be prepared by binding a drug other than any of the above examples to an antibody in accordance with the method for binding a toxin or cytotoxic agent to an antibody.

<Pharmaceutical Composition>

The present invention also provides a pharmaceutical composition for cancer treatment, which comprises the molecular-targeted anticancer agent in combination with a pharmaceutically acceptable carrier.

The molecular-targeted anticancer agent of the present invention is capable of inhibiting the metastasis (and in particular, lymph node metastasis or hematogenous metastasis), in addition to inhibition of the growth of cancer cells and cancer-related macrophages. Through inhibition of such metastasis, neoplasm metastasis to different organs can be inhibited.

Since the molecular-targeted anticancer agent of the present invention binds specifically to, for example, the FRβ-expressing macrophages (Patent Document 4) existing at the invasive front of invasive pancreatic cancer and the pancreatic cancer cells, pancreatic cancer can be selectively attacked, and the influence imposed on normal cells can be minimized.

A pharmaceutically acceptable carrier (or an excipient) may be liquid or solid, and an adequate carrier can be selected in accordance with a type of an oral or parenteral preparation. Examples thereof include sterile water, buffer such as PBS, physiological saline, Ringer's solution, ethanol, glycerol, vegetable oil, gelatin, sucrose, lactose, amylose, starch, fatty acid ester, and hydroxymethylcellulose. In addition to such carrier, the pharmaceutical composition can further comprise an adjuvant, such as a lubricant, preservative, stabilizer, wetting agent, emulsifier, disintegrator, solubilizer, isotonizing agent, binder, buffer, or colorant, according to need.

The pharmaceutical composition of the present invention can be administered orally, intravenously, intraarterially, transmucosally, intramuscularly, subcutaneously, buccally, intraperitoneally, intraarticularly, intrasynovially, sternally, intranasally, or via bolus injection, continuous injection, or direct delivery to the lesion.

The pharmaceutical composition is formulated in accordance with the route of administration. Examples of dosage forms include, but are not particularly limited to, injection preparations, solutions, suspensions, tablets, granules, powders, sprayers, capsules, enteric preparations, controlled-release agents, and multiple-layer preparations.

The molecular-targeted anticancer agent, which is an active ingredient of the pharmaceutical composition of the present invention, is integrated into a unit dosage form in a therapeutically effective amount. A dose can be altered in accordance with a variety of factors, such as sexuality, age, and body weight of a subject, the severity, the route of administration, and side effects. The amount of active ingredients is about 1 µg or more per day (e.g., at least 50 µg to 100 µg), although the amount is not limited thereto. Administration may be either a single administration or multiple administrations.

The pharmaceutical composition of the present invention can be administered in combination with a conventional therapeutic agent for cancer. Examples of conventional therapeutic agents include pharmaceuticals, such as gemcitabine, 5-FU, cisplatin, Gemzar, and TS-1. Such therapeutic agents can be administered to a subject, prior to, simultaneously with, or following the administration of the pharmaceutical composition of the present invention.

Further, the present invention relates to a method for treating cancer, comprising administering a therapeutically effective amount of the anti-FRα/β antibody, molecular-targeted anticancer agent, or pharmaceutical composition for cancer treatment of the present invention to a cancer patient.

<Methods for Detecting the Presence of Cancer or the Degree of Malignancy of Cancer, Methods for Determining Therapeutic Effects of Cancer Treatment, and Cancer Diagnostic Agents and Kits Used for Such Methods>

Another aspect of the present invention provides a method for detecting (examining) the presence of cancer or the degree of malignancy of cancer based on the presence of FRα-expressing cancer cells and FRβ-expressing cancer-related macrophages, comprising bringing a subject-derived biological sample (e.g., a tissue or cell sample) into contact with the anti-FRα/β antibody (i.e., an antibody (cancer diagnostic agent) labeled with a fluorophore, pigment, or radioactive isotope or an non-labeled antibody) of the present invention.

For example, a subject-derived pancreatic cancer tissue sample is brought into contact with the anti-FRα/β antibody (i.e., an antibody labeled with a fluorophore, pigment, radioactive isotope, or the like (cancer diagnostic agent) or a non-labeled antibody) of the present invention to examine whether or not FRα-expressing pancreatic cancer cells are present and whether or not FRβ-expressing macrophages are present in the vicinity of pancreatic cancer cells at the invasive front of the tissue. If FRα-expressing pancreatic cancer cells are present and FRβ-expressing macrophages are distributed around pancreatic cancer cells at the invasive front, it is determined that the tissue is invasive and metastatic. Thus, the degree of malignancy of pancreatic cancer or whether or not invasive pancreatic cancer is present can be examined. The term "invasion" or "infiltration" as used herein refers to the situation in which the tumor departs from the deep part of the lesion tissue, and from the primary lesion, as tumor cell motility is enhanced. When a tumor is determined to be invasive, the tumor has become metastatic and malignant. As disclosed in Patent Document 4, there is a correlation between the pancreatic cancer front becoming invasive and FRβ-expressing macrophages accumulating. By detecting the presence of FRα-expressing pancreatic cancer cells and FRβ-expressing macrophages with the use of the antibody or a fragment thereof, the pancreatic cancer of interest is determined (judged, identified, classified, or evaluated) to be invasive and metastatic.

Another aspect of the present invention provides a method for determining therapeutic effects of cancer treatment based on the presence or absence of FRα-expressing cancer cells and FRβ-expressing cancer-related macrophages, comprising bringing a cancer tissue sample obtained from a subject who is receiving or has received cancer treatment into contact with the anti-FRα/β antibody (i.e., an antibody (cancer diagnostic agent) labeled with a fluorophore, pigment, or radioactive isotope or an non-labeled antibody) of the present invention.

The term "determine" as used herein does not intend to refer to a judgment made by a doctor (i.e., medical act), but the term refers to a means for assisting a doctor in making decisions through presentation of the information or data concerning the examination results to a doctor. Accordingly, the term "determine" should be used interchangeably with the term, such as "measure," "examine," "judge," or "evaluate."

In addition, the present invention provides a cancer diagnostic agent or a cancer diagnostic kit used for the above detection or examination methods and the like.

In the case of imaging diagnosis, the cancer diagnostic agent or the cancer diagnostic kit can comprise a conjugate of the antibody or a fragment thereof and a label. Examples of labels include a fluorophore, a pigment, and a radioactive isotope as exemplified above.

Detection of FRα-expressing cancer cells and FRβ-expressing macrophages with the use of antibodies can be performed via, for example, ELISA, fluorescent antibody methods, radioimmunodetection, sandwich methods, or histological tissue staining. Labels, such as enzymes (e.g., peroxidase or alkaline phosphatase), fluorophores (e.g., FITC, tetramethylrhodamine, or Texas Red), pigments, or radioactive isotopes, are conjugated to secondary antibodies, and conjugates of antibodies bound to cancer cells and macrophages are detected. Examples of label binding include chemical binding and biotin-(strepto)avidin-based binding.

In the case of the imaging diagnosis, antibodies are labeled with pharmaceutically acceptable radioactive nuclides or luminophores, the resulting antibodies are administered to a subject, images are generated through diagnostic imaging techniques, such as PET/CT, and the presence of cancer can be determined or detected.

The cancer diagnostic kit of the present invention can comprise, in addition to the (labeled or non-labeled) antibodies mentioned above or fragments thereof and contrast media comprising the same, a buffer used for measurement, reagents (e.g., labeled secondary antibodies), instructions for measurement procedures, and the like. Reagents are hermetically sealed in separate containers.

With the use of the aforementioned anti-FRα/β antibody or a substance to which the antibody is bound according to the present invention, it is possible to effectively treat cancer by simultaneously damaging FRα-expressing cancer cells and FRβ-expressing cancer-related macrophages to a greater degree than is possible with the conventional monotherapy with an anti-FRα antibody targeting cancer cells or an anti-FRβ antibody targeting cancer-related macrophages that promote cancer growth. Further, it is also possible to determine the presence or absence of various cancers, the degree of malignancy, and therapeutic effects of cancer treatment, all of which are advantageous in the medical industry.

In addition, in the case of the conventional combined therapy involving two agents (i.e., an anti-FRα antibody and an anti-FRβ antibody), it would be difficult to determine appropriate doses of the anti-FRα antibody and the anti-FRβ antibody because of the difference between the binding of the anti-FRα antibody to FRα-expressing cancer cells and the binding of the anti-FRβ antibody to FRβ-expressing macrophages. Meanwhile, the dose of the anti-FRα/β antibody or the substance to which the antibody is bound according to the present invention can be reduced to a level lower than that in the combination therapy of the anti-FRα antibody and the anti-FRβ antibody, which is economically advantageous.

Hereafter, the present invention is described in greater detail with reference to Examples, although the technical scope of the present invention is not limited thereto.

EXAMPLE 1

Preparation of Anti-Human FRα/β Rat Monoclonal Antibody (Clone Name: No. 5)

[Preparation of Human FRβ-Expressing Cells]

Total RNA was extracted from the articular rheumatism synovial membrane using Trizol (GibcoBRL) and the cDNA synthesis kit (Invitrogen) in accordance with the manufacturer's instructions, and cDNA was then synthesized using the SuperScript plasmid System (Invitrogen) in accordance with the manufacturer's instructions. Subsequently, 1 μl of cDNA derived from the rheumatism synovial membrane was added to the Bioneer PCR premix (Bioneer), the sense primer (agaaagacatgggtctggaaatggatg (SEQ ID NO: 21)) and the antisense primer (catatggactgaactcagccaaggagcca-gagtt (SEQ ID NO: 22)) adjusted to 10 pmol were added, and PCR was carried out through 30 cycles of 94° C. for 20 seconds, 58° C. for 30 seconds, and 72° C. for 60 seconds, followed by the reaction at 72° C. for 5 minutes, to amplify the human FRβ gene. The PCR product of the amplified FRβ gene was ligated to the PCR2.1-TOPO plasmid (Invitrogen). Specifically, 1 μl of a NaCl solution, 1.5 μl of sterile distilled water, and 1 μl of the plasmid vector (PCR2.1-TOPO) were added to 2.5 μl of the PCR product, the mixture was incubated at room temperature for 5 minutes, 2 μl of the product was added to E. coli cells (TOP10F'), the resultant was subjected to the reaction on ice for 30 minutes, it was subjected to thermal treatment at 42° C. for 30 seconds, the resultant was allowed to stand on ice for 2 minutes, 250 µl of SOC medium was added thereto, and the resultant was cultured in a shaker at 37° C. for 1 hour. After the completion of culture, the culture product was seeded on an LB medium, and culture was conducted at 37° C. overnight.

In order to culture *E. coli* cells, white colonies sampled from the plate were applied to LB liquid medium containing 50 mg/ml ampicillin to conduct culture at 37° C. overnight. Plasmids in *E. coli* cells were purified using the Qiagen plasmid purification kit (Qiagen). The integrated FRβ gene was treated with the restriction enzyme EcoRI and then developed into agarose electrophoresis. After the FRβ gene product of about 0.8 kb (782 bp) was detected, the site was cut out, and the extracted gene product was purified using the Qiagen PCR purification kit (Qiagen). Subsequently, the resultant was mixed with the mammalian cell expression vector, which had been treated with EcoRI in advance (pER-BOS, Mizushima et al. pEF-BOS, a powerful mammalian expression vector, Nucleic Acid Res. 1990; 18 (17): 5322), and ligation was carried out using the T4 ligase (Roche). The ligation product was transduced into the *E. coli* cells (TOP10F') and the FRβ gene was detected in the manner described above.

After the FRβ gene integrated into pEF-BOS was confirmed, a vector comprising the human FRβ gene was transduced into the mouse B300-19 cells. Specifically, a mixture of 20 µl of lipofectamine (GibcoBRL) with 1 µg of the vector comprising the FRβ gene was added to each of the cells adjusted to a density of $1\times10^5$ cells. In order to acquire antibiotic G418-tolerance, the transduced mouse B300-19 cells were subjected to selective culture in a medium containing G418 at 1 mg/ml. Introduction of the FRβ gene into the transduced cells was confirmed via PCR. Specifically, cDNA was synthesized from the adjusted $1\times10^7$ cells using the cDNA synthesis kit (Invitrogen), the sense primer (agaaagacatgggtctggaaatggatg (SEQ ID NO: 21)) and the antisense primer (catatggactgaactcagccaaggagccagagtt (SEQ ID NO: 22)) adjusted to 10 pmol were added to the Bioneer PCR premix (Bioneer). PCR was carried out through 30 cycles of 94° C. for 20 seconds, 58° C. for 30 seconds, and 72° C. for 60 seconds, followed by the reaction at 72° C. for 5 minutes, to amplify the human FRβ gene. Thereafter, agarose electrophoresis was carried out to confirm a 0.8-kb band indicated by the FRβ gene.

[Preparation of Monoclonal Antibody Reacting to Both Human FRα and Human FRβ]

The human FRβ-expressing mouse B300-19 cells were adjusted at $1\times10^7$ cells, the cells were mixed with the complete Freund's adjuvant, and Whister Kyoto rats were immunized therewith through the tail root or intraperitoneally. This procedure was repeated 2 to 4 times every week.

Monoclonal antibodies were produced by the Koler's method (Kohler & Milstein, Nature, 1975, 256: 495-96). Specifically, the spleens or iliac lymph nodes were removed and dissociated into single cells, and the resultant was fused to myeloma-derived cells (NS-1) to prepare hybridomas. Hybridomas were cultured in a HAT selection medium, and antibodies secreted into the culture supernatant were selected based on the reactivity with both the FRβ-expressing cells and the FRα-expressing KB cell line (Human epidermoid carcinoma).

Hybridomas that were found to produce antibodies were subjected to cloning by limiting dilution culture diluted to 1 cell/well in a 96-well plate.

Antibodies were collected by culturing the cloned hybridomas in IMDEM medium (Gibco) containing 10% FCS, 10% NCTC-109 medium (Gibco), 1% HT Supplement (Gibco), and 1% Antibiotic/Antimycotic Mixed (Nakarai), followed by purification with goat anti-rat immunoglobulin agarose (Rockland).

Thus, the anti-human FRα/β rat monoclonal antibody (clone name: No. 5) (hereafter referred to as "antibody No. 5") was obtained.

[Experimentation to Cause Antibody No. 5 to React with FRα and FRβ Using Flow Cytometer (FACS)]

FR-β-expressing B300-19 cells (FIG. 2 (A)) and FRα-expressing KB cells (FIG. 2 (B)) adjusted to $1\times10^5$ cells were reacted with antibody No. 5. Also, the cells were reacted with positive control antibodies, which were an antibody recognizing FRβ (94b) (Patent Document 4) and an antibody recognizing FRα (Mov18) (Miotti S, Canevari S, Menard S, Mezzanzanica D, Porro G, Pupa S M, Regazzoni M, Tagliabue E, Colnaghi M I., Characterization of human ovarian carcinoma-associated antigens defined by novel monoclonal antibodies with tumor-restricted specificity. Int J Cancer. 1987; 39 (3): 297-303.), and a negative control antibody, which was isotype control RatIgG2a (Southern Biotech). The cells were further reacted with an anti-rat antibody labeled with APC. After the end of reaction, stainability was determined using a flow cytometer.

As shown in FIG. 2, antibody No. 5 reacted with both the FR-β-expressing B300-19 cells and the FRα-expressing KB cells.

Then, ovarian cancer IGROV1, OVACAR3, and SKOV3 cell lines were reacted with antibody No. 5. The cell lines were also reacted with a positive control antibody, which was an antibody recognizing FRα (Mov18), and a negative control antibody, which was isotype control RatIgG2a (Southern Biotech). The cell lines were further reacted with an anti-rat antibody labeled with APC. After the end of reaction, stainability was determined using a flow cytometer.

As shown in FIG. 3, antibody No. 5 showed a strongly positive reaction to IGROV1, compared with the Mov18 antibody, but it did not show a reaction to OVACAR3, to which the Mov18 antibody showed a reaction, suggesting that these antibodies bind to different epitopes.

[Immunostaining of Ovarian Cancer Tissue with Antibody No. 5]

Cancer tissue obtained from ovarian cancer patients was reacted with antibody No. 5, the anti-FRα antibody (Mov18), the anti-FRβ antibody (94b), and the anti-CD68 antibody. The tissue was further reacted with a peroxidase-labeled anti-rat IgG antibody or a peroxidase-labeled anti mouse IgG antibody and then color-developed with a DAB color development reagent (DAKO).

Figure 4:
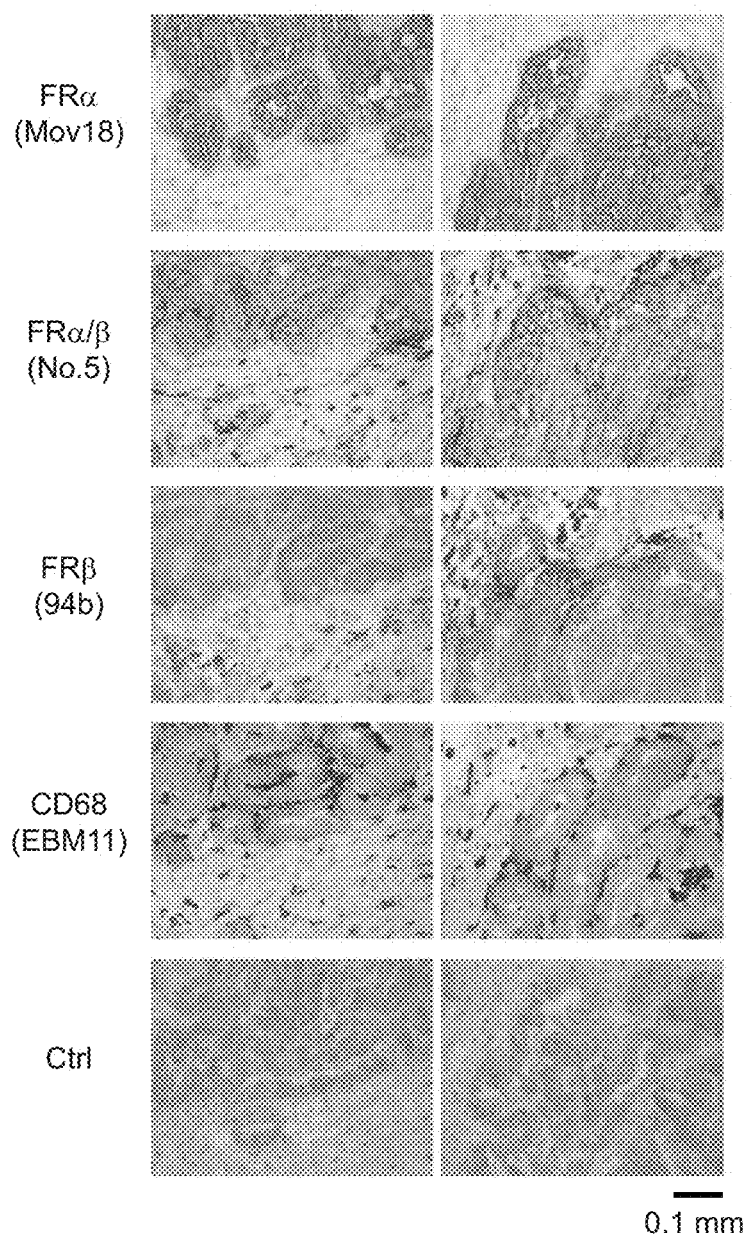
FIG. 4 shows immunostaining results indicating reactivity of the anti-human FRα/β rat monoclonal antibody to ovarian cancer tissue.

FIG. 4 shows staining patterns of two sites of an identical specimen stained with each antibody. Antibody No. 5 was found to react with FRα-positive cancer cells and FRβ (+) macrophages infiltrating cancer tissue.

[Complement-Dependent Cytotoxicity of Antibody No. 5 on Folate Receptor-Expressing Cells]

IGROV cells, ES-2 cells, and human FRβ-expressing B300-19 cells adjusted to $5\times10^4$ cells/50 µL in RPMI medium were seeded in each well of a 96-well plate. Then, antibody No. 5 or an anti-GFP antibody used as a negative control, which was adjusted to a concentration of 1 µg/25 µL with RPMI medium, or 25 µL of RPMI medium was added to each well. Next, 25 µL of rabbit complement serum diluted to 50% with RPMI medium (Sigma-Aldrich Co. LLC.) or 25 µL of RPMI medium was added (to result in $5\times10^4$ cells/100 µL per well, a final concentration of each antibody of 10 µg/mL, and a final concentration of the complement of 12.5%). Cells to which 50 µL of RPMI medium had been added were used for an antibody-free control group (baseline group). Further, a cell-number-based dilution series was prepared for the baseline group. Cells to which 50 μL of RPMI medium containing 2% Triton X-100 had been added were used for a positive control group (maximum cytotoxicity group). Four wells of each group set above were used for culture in a $CO_2$ incubator (37° C.) for 2 hours. After the completion of culture, cell counting kit-8 (Dojindo Laboratories) was added to each well, and absorbance (450 nm) shown by viable cells in the culture solution was measured using a microplate reader (Bio-Rad Laboratories). The decrease in absorbance of the cell-number-based dilution series of the baseline group and absorbance of the Triton X-100 addition group (maximum cytotoxicity group) were plotted and then the cytotoxicity rate was calculated based on the absorbance of each well.

Figure 5:
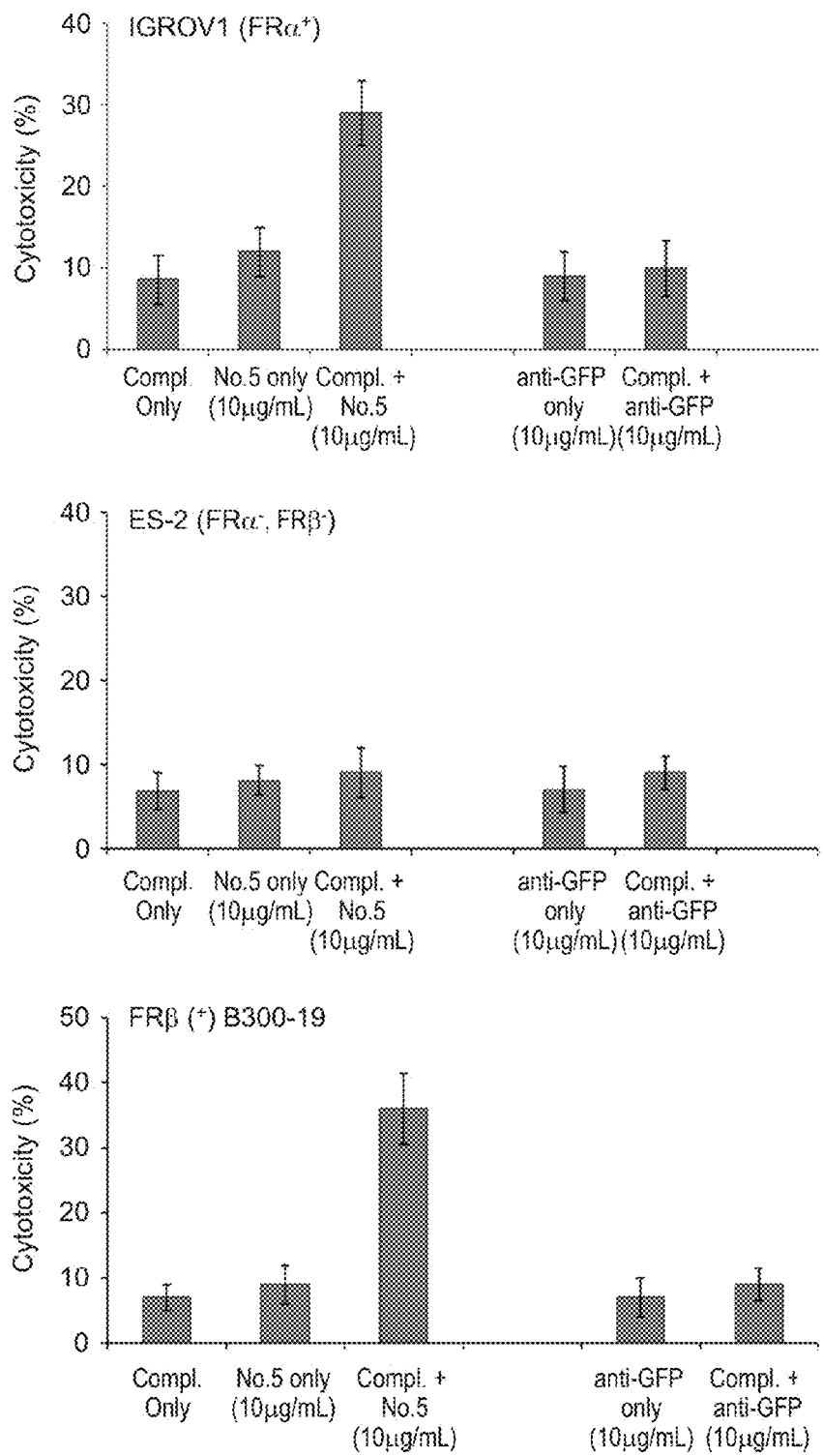
FIG. 5 shows the complement-dependent cytotoxicity levels of the anti-human FRα/β rat monoclonal antibody in folate-receptor-expressing cells.

As shown in FIG. 5, the anti-human FRα/β antibody showed cytotoxicity to the FRα-expressing cell line (upper chart) and the FRβ-expressing cell line (lower chart) in the presence of the complement while it did not show cytotoxicity to the cell line expressing neither FRα nor FRβ (middle chart) even in the presence of the complement. The results suggest that the anti-human FRα/β antibody has the ability to inhibit proliferation of FRα-expressing cancer cells in vivo in the presence of the complement.

EXAMPLE 2

Preparation of Anti-Human FRα/β Immunotoxin (Molecular-Targeted Drug) from Antibody Gene of Antibody No. 5

[Determination of Antibody Gene of Antibody No. 5]

A rat hybridoma clone No. 5, which produces antibody No. 5, was adjusted to 1×10$^7$ cells, and cDNA was synthesized using the cDNA synthesis kit (Invitrogen). Subsequently, the heavy chain (hereafter referred to as "VH") and light chain (hereafter referred to as "VL") genes were amplified via PCR using the Ig-Prime Kit and the primer (caccatggagttacttttgag (SEQ ID NO: 23)) designed for cloning the rat antibody heavy chain region.

The PCR amplification products of the VH and VL genes were ligated to the PCR2.1-TOPO plasmid (Invitrogen) and the resultant was transduced into *E. coli* (TOP10F'). Subsequently, plasmids were purified from *E. coli*, and the nucleotide sequences of the VH and VL genes were determined. The nucleotide sequences were determined by performing PCR using the BigDye Terminaor V3.1 cycle sequencing kit (ABI) and analyzed using the ABI 310 DNA sequencer.

As described above, the following genes were determined as the antibody genes of antibody No. 5: the VH gene (the nucleotide sequence: SEQ ID NO: 7; and the corresponding amino acid sequence: SEQ ID NO: 8), the CDRH1 gene (the nucleotide sequence: SEQ ID NO: 1; and the corresponding amino acid sequence: SEQ ID NO: 2), the CDRH2 gene (the nucleotide sequence: SEQ ID NO: 3; and the corresponding amino acid sequence: SEQ ID NO: 4), and CDRH3 gene (the nucleotide sequence: SEQ ID NO: 5; and the corresponding amino acid sequence: SEQ ID NO: 6); and the VL gene (the nucleotide sequence: SEQ ID NO: 15; and the corresponding amino acid sequence: SEQ ID NO: 16), the CDRL1 gene (the nucleotide sequence: SEQ ID NO: 9; and the corresponding amino acid sequence: SEQ ID NO: 10), the CDRL2 gene (the nucleotide sequence: SEQ ID NO: 11; and the corresponding amino acid sequence: SEQ ID NO: 12), and the CDRL3 gene (the nucleotide sequence: SEQ ID NO: 13; and the corresponding amino acid sequence: SEQ ID NO: 14) (FIG. 1).

[Introduction of Cysteine Mutation into Immunoglobulin Heavy Chain Variable Region (VH) Gene]

Primers (sense: agcctccgggaaagtgtctggagtggatg (SEQ ID NO: 24); and antisense: catccactccagacactttcccggaggct (SEQ ID NO: 25)) were designed so as to cause mutation of a codon (the nucleotide sequence: ggt) corresponding to glycine at amino acid 44 with a codon (the nucleotide sequence: tgt) corresponding to cysteine in the amino acid sequence (SEQ ID NO: 8) corresponding to the immunoglobulin heavy chain variable region (VH) gene (SEQ ID NO: 7) of antibody No. 5, and the pCR2.1-TOPO VH plasmid comprising the VH gene of antibody No. 5 was subjected to mutagenesis using the Quick change site-directed mutagenesis kit (Stratagene). PCR was carried out through 12 continuous cycles of 95° C. for 30 seconds, 55° C. for 60 seconds, and 68° C. for 4 minutes.

Subsequently, DNA was transduced into *E. coli* XL1-Blue after the reaction, and selective culture was conducted in an LB medium containing ampicillin at 0.1 mg/ml. Plasmids of the selected transformants were purified using the QIAprep spin Miniprep Kit (Qiagen). Further, the nucleotide sequence was determined using the BigDye Terminaor V3.1 cycle sequencing kit (ABI) and the ABI 310 DNA sequencer, and mutation of glycine 44 in VH (SEQ ID NO: 8) of antibody No. 5 with cysteine (the nucleotide sequence: tgt) was confirmed. The obtained nucleotide sequence of the mutated VH gene is the nucleotide sequence of SEQ ID NO: 17, and the corresponding amino acid sequence is the amino acid sequence of SEQ ID NO: 18.

[Insertion of Mutated VH into Protein-Expressing pRK79PE38 Vector]

Subsequently, the mutated VH gene (SEQ ID NO: 17) resulting from mutation of the VH gene of antibody No. 5 was inserted into the pRK79 vector (pRK79PE38) containing the PE38 gene (Kreitman R J, Bailon P, Chaudhary V K, FitzGerald D J, Pastan., Recombinant immunotoxins containing anti-Tac (Fv) and derivatives of *Pseudomonas* exotoxin produce complete regression in mice of an interleukin-2 receptor-expressing human carcinoma. Blood. 1994 Jan. 15; 83 (2): 426-34) in the manner described below.

For annealing of the 5' end and the 3' end of the mutated VH gene, the primers catatgcaggtgcagctgaaggag (SEQ ID NO: 26) and ggaagcttttgaggagactgtgaccatga (SEQ ID NO: 27) were designed. The set of primers for annealing comprises the site for the NdeI restriction enzyme, and cloning at this site enables protein expression using atg as an initiation codon. The HindIII site has been inserted into another primer, and cloning at this site enables expression of a fusion protein of the mutated VH gene and the PE gene.

The plasmid into which mutation had been introduced with the use of such set of primers and pfu DNA polymerase (Stratagene) was subjected to PCR. PCR was carried out through 30 cycles of 94° C. for 20 seconds, 55° C. for 30 seconds, and 72° C. for 60 seconds, followed by the reaction at 72° C. for 5 minutes. Subsequently, the PCR product was purified, and the NdeI and HindIII (New England Biolabs) restriction enzymes were added to the purified product. After the reaction, the resultant was subjected to electrophoresis, and DNA of the target size was recovered from the gel using the QIAquick gel extraction kit (Qiagen). To the recovered DNA, pRK79PE38 treated with the same restriction enzymes as the mutated VH gene treated with the restriction enzymes was added, and mutated VH gene and pRK79PE38 were subjected to ligation using Ligation High (Toyobo).

After the completion of ligation, *E. coli* TOP10F' (Invitrogen) was transduced, and transformants were selected in an LB medium containing ampicillin at 0.1 mg/ml. The pRK79-VHPE plasmids of the selected transformants were purified using the QIAprep spin Miniprep Kit (Qiagen). Further, the nucleotide sequence was determined using the BigDye Terminaor V3.1 cycle sequencing kit (ABI) and the ABI 310 DNA sequencer (rat anti-human FRα/β immunotoxin VHPE comprising mutated VH (SEQ ID NO: 18)).

[Introduction of Cysteine Mutation into Immunoglobulin Light Chain Variable Region Gene]

Primers (catatggacatccagatgacacagtct (SEQ ID NO: 28) and gaattcctatttcaattccagcttggtgccacaaccgaacgt (SEQ ID NO: 29)) were designed so as to cause mutation of a codon (the nucleotide sequence: gga) corresponding to glycine at amino acid 100 with a codon (the nucleotide sequence: tgt) corresponding to cysteine in the amino acid sequence (SEQ ID NO: 16) of the immunoglobulin light chain variable region (VL) gene (SEQ ID NO: 15) of antibody No. 5.

The plasmid containing the VL gene of antibody No. 5 was subjected to PCR with the use of such set of primers and pfu DNA polymerase (Stratagene). PCR was carried out through 30 cycles of 94° C. for 20 seconds, 55° C. for 30 seconds, and 72° C. for 60 seconds, followed by the reaction at 72° C. for 5 minutes. Subsequently, the PCR product was purified, and the NdeI and EcoRI (New England Biolabs) restriction enzymes were added to the purified product. After the reaction, the resultant was subjected to electrophoresis, and DNA of the target size was recovered from the gel using the QIAquick gel extraction kit (Qiagen). To the recovered DNA, pRK79PE38 treated with the same restriction enzymes as the mutated VL gene treated with the restriction enzymes was added, and the mutated VL gene and pRK79PE38 were subjected to ligation using Ligation High (Toyobo). After the completion of ligation, *E. coli* TOP10F' (Invitrogen) was transduced, and transformants were selected in an LB medium containing ampicillin at 0.1 mg/ml. The pRK79-VL plasmids of the selected transformants were purified using the QIAprep spin Miniprep Kit (Qiagen). Further, the nucleotide sequence was determined using the BigDye Terminaor V3.1 cycle sequencing kit (ABI) and the ABI 310 DNA sequencer, and mutation of amino acid 100 of VL (SEQ ID NO: 16) of antibody No. 5 with cysteine and the provision of the termination codon (tag) were confirmed (rat anti-human FRα/β immunotoxin VL comprising mutated VL (the nucleotide sequence: SEQ ID NO: 19; the corresponding amino acid sequence: SEQ ID NO: 20)).

[Preparation of Recombinant Protein Inclusion Body]

The pRK79-VHPE plasmid into which the mutated VH gene had been integrated and the pRK79-VL plasmid into which the mutated VL gene had been integrated (50 ng each) were prepared, and the plasmids were transduced into protein-expressing *E. coli* BL21 (DE3). The transduced *E. coli* was selected through culture in an LB medium containing ampicillin at 0.1 mg/ml at 37° C. for 15 to 18 hours.

After the completion of selection, *E. coli* was cultured in 1,000 ml Super broth medium at 37° C., and culture was continued until the visible-light absorption at 600 nm reached 1.0 to 1.5. Thereafter, IPTG (isopropyl-beta-D-thiogalactopyranoside) was added to the medium to result in the final concentration of 1 mM, and culture was further conducted at 37° C. for 90 minutes. After the completion of culture, *E. coli* cells were recovered via centrifugation, and 200 ml of a suspension thereof was prepared with the use of 50 mM Tris buffer (pH 7.4, containing 20 mM EDTA). Thereafter, egg white lysozyme was added to a final concentration of 0.2 mg/ml, the reaction was allowed to proceed at room temperature for 1 hour to destroy *E. coli* cells. Thereafter, the resultants were centrifuged at 20,000×g, and the precipitate was recovered. The precipitate was further suspended in 50 mM Tris buffer (pH 7.4, containing 2.5% Triton X-100, 0.5 M NaCl, and 20 mM EDTA) to adjust the amount of the solution to 200 ml, egg white lysozyme was added to a final concentration of 0.2 mg/ml, and the reaction was allowed to proceed at room temperature for 1 hour. After the completion of the reaction, the reaction product was centrifuged at 20,000×g, and the precipitate was recovered. Thereafter, the precipitate was suspended to 200 ml with 50 mM Tris buffer (pH 7.4, containing 2.5% Triton X-100, 0.5 M NaCl, and 20 mM EDTA), and then was thoroughly mixed and centrifuged at 20,000×g, and the precipitates were then recovered. This procedure was repeated 5 times, and the resulting precipitate, which was a recombinant immunotoxin inclusion body, was further dissolved in 0.1M Tris buffer (pH 8.0, containing 6 M guanidine hydrochloride and 1 mM EDTA) to adjust it to the final concentration to 10 mg/ml.

[Coupling of Solubilized VHPE and VL, Refolding, and Purification]

VHPE was mixed with VL to produce the recombinant double-chain Fv anti-FRα/β immunotoxin.

At the outset, 0.5 ml of VHPE was admixed with 0.25 ml of VL, dithiothreitol (DTT) was added to a final concentration of 10 mg/ml, and the resultant was subjected to reduction at room temperature for 4 hours. After reduction, the resultant was dissolved in 75 ml of 0.1 M Tris buffer (pH 8.0, containing 0.5 M arginine, 0.9 mM oxidized glutathione, and 2 mM EDTA). The resulting solution was allowed to stand at 10° C. for 40 hours to bind VH to VL. After the completion of binding, the solution was concentrated to the amount of 5 ml with the use of a centrifugal concentrator with the molecular-weight cut-off 10,000 (Centricon 10, Amicon), and the concentrate was then diluted with 50 ml of Tris buffer (pH 7.4, containing 0.1 M urea and 1 mM EDTA). The diluted solution was used as a starting material for purification of the recombinant immunotoxin.

Subsequently, the starting material was allowed to adsorb to an ion-exchange column (Hi-Trap Q, GE) equilibrated with Tris buffer (pH 7.4, containing 1 mM EDTA) at the flow rate of 30 ml/hr, followed by washing with Tris buffer (pH 7.4, containing 1 mM EDTA). Thereafter, the adsorbed recombinant immunotoxin was eluted with Tris buffer (pH 7.4, containing 0.3 M NaCl and 1 mM EDTA). The eluted sample was dialyzed against Tris buffer (pH 7.4, containing 1 mM EDTA) and further purified through an ion-exchange column (POROS HQ, POROS). Specifically, the dialyzed and purified substance was allowed to adsorb to the column at the flow rate of 10 ml/min, the column was washed with Tris buffer (pH 7.4, containing 1 mM EDTA), and elution of the recombinant immunotoxin was carried out with a NaCl gradient of 0 M to 1.0 M in the buffer. The final product of the purified recombinant immunotoxin was prepared via gel filtration chromatography (TSK300SW, Tosoh). At the outset, endotoxin was removed from the TSK300SW column by washing with 75% ethanol for disinfection for 48 hours. Subsequently, the TSK300SW column was washed with distilled water for injection according to the Japanese Pharmacopoeia and then equilibrated with physiological saline according to the Japanese Pharmacopoeia. After the completion of equilibration, the recombinant immunotoxin was administered, and the eluate from the column was obtained at the flow rate of 0.25 ml/min. Thereafter, the eluate was applied to a 0.22-μm filter sterilizer, the purity was determined by SDS-PAGE, and the resultant was then stored at −80° C.

[Purity Determined by SDS-PAGE]

SDS-PAGE (electrophoresis on polyacrylamide gel containing sodium dodecyl sulfate) was carried out using a 12% polyacrylamide flat gel containing 0.1% sodium dodecyl sulfate (SDS) and, as a mobile phase, an aqueous solution comprising SDS (final concentration: 0.1%), 130 mM glycine, and 25 mM Tris. The sample was adjusted with 100 mM Tris buffer (pH 6.5) containing SDS (final concentration: 0.1%) and subjected to boiling for 5 minutes. After the completion of boiling, the sample was applied to the flat gel and electrophoresis was carried out at the constant current of 30 mA. Thereafter, the recombinant immunotoxin was stained with a solution of 0.05% Coomassie brilliant blue R (Nacalai Tesque).

EXAMPLE 3

Inhibition of Growth of Ovarian Cancer (IGROV1 Cell Line) and FRβ-Expressing Cells Caused by Recombinant Immunotoxin The human ovarian cancer IGROV1 cell line and human FRβ-expressing B300-19 cells adjusted to $2.5 \times 10^5$ cells/mL were seeded in each well of a 24-well plate. Further, the recombinant anti-human FRα/β immunotoxin prepared in Example 2 or VH-PE used as a negative control protein was adjusted to a final concentration of 2000-0 ng/mL and added to each well, followed by culture for 48 hours to 96 hours. After the completion of culture, cell counting kit-8 (Dojindo Laboratories) was added to each well and the absorbance of the culture solution was determined using a microplate reader (Bio-Rad Laboratories).

Figure 6:
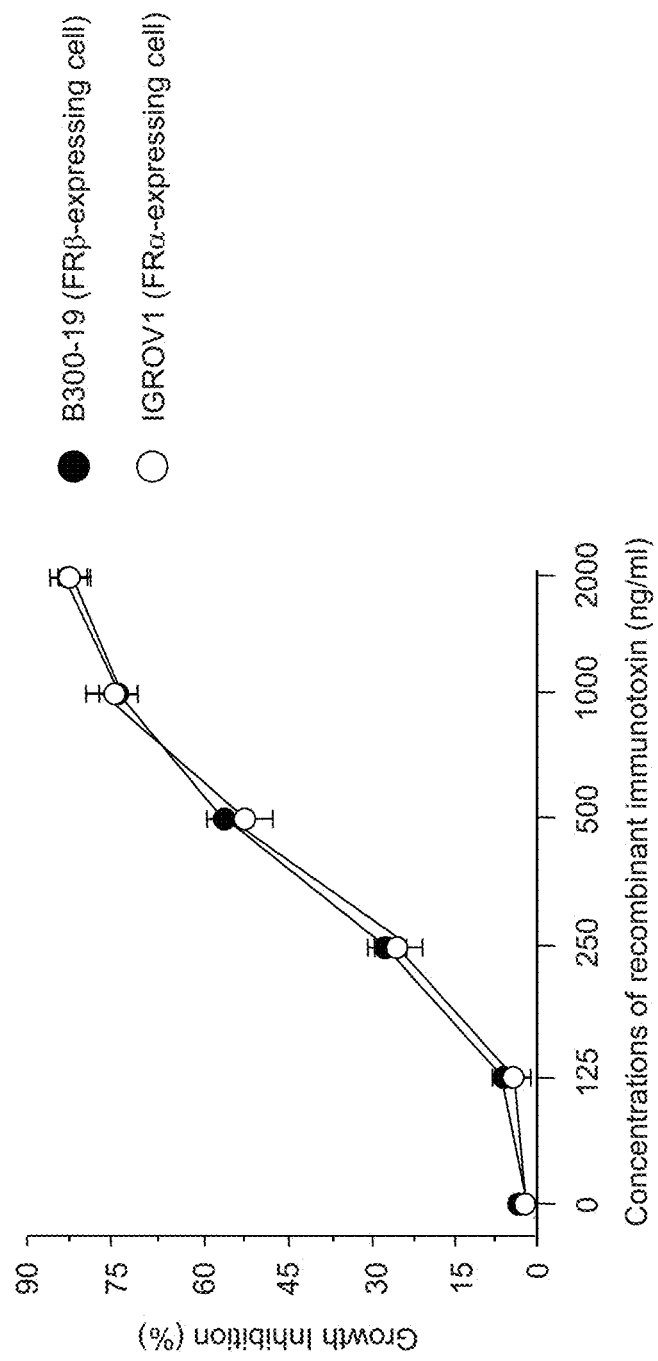
FIG. 6 is a graph showing growth inhibitory effects of the anti-human FRα/β immunotoxin upon the human ovarian cancer cells (FRα-expressing cell line) and the human FRβ-expressing cells.

FIG. 6 shows the results. As shown in FIG. 6, the recombinant anti-human FRα/β immunotoxin showed cytotoxicity to both the FRα-expressing cell line and the FRβ-expressing cell line. The results suggest that a drug having cytotoxicity to which the anti-human FRα/β antibody is bound is useful as a molecular-targeted drug for FRα-expressing cancer.

EXAMPLE 4

Immunostaining of Lung Cancer, Breast Cancer, and Pancreatic Cancer with Antibody No. 5

Cancer tissues obtained from lung cancer, breast cancer, and pancreatic cancer patients were reacted with an antibody against FRα (reactive to cancer cells), antibody No. 5, and an antibody against FRβ (reactive to macrophages) and with peroxidase-labeled anti-rat IgG or the peroxidase-labeled anti-mouse IgG antibody, and then color-developed with a DAB color development reagent (DAKO).

Figure 7:
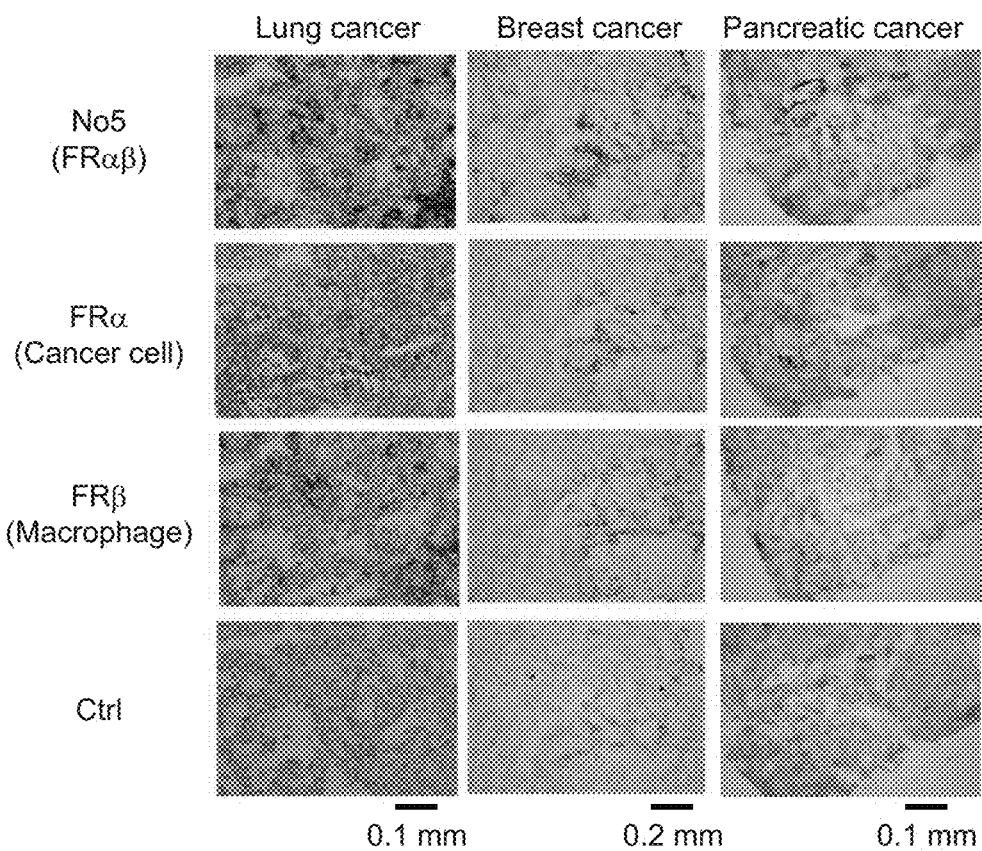
FIG. 7 shows staining patterns obtained by immunostaining of different solid cancers with the anti-human FRα/β rat monoclonal antibody.

FIG. 7 shows immunostaining patterns of the antibodies against the respective solid cancers. Antibody No. 5 was found to react with cancer cells and infiltrating macrophages in 6 out of 19 cases of lung cancer, 4 out of 14 cases of breast cancer, and 2 out of 3 cases of pancreatic cancer.

EXAMPLE 5

Assessment of Antibody No. 5 Promoting Capacity of Macrophages to Phagocytize Folate Receptor α-Expressing Cancer Cells (Analysis by ADCP (Antibody-Dependent Cell Mediated Phagocytosis) Method)

Blood (50 ml) was sampled from a healthy individual using a heparin-containing syringe. The sampled blood was diluted threefold with phosphate buffer (pH 7.4 (PBS)) and then the diluted blood was layered on 15 ml of a Lymphoprep solution (Fresenius Kabi Norge A S) contained in a 50-ml Falcon tube, followed by centrifugation for 15 minutes at 2500 rpm with automatic deceleration. Subsequently, a layer containing monocytes and lymphocytes was collected and mixed with three parts of PBS, followed by centrifugation at 1500 rpm for 8 minutes. After centrifugation, the supernatant was discarded, the remaining pellets were crushed, and 50 ml of PBS was added thereto, followed by centrifugation at 800 rpm for 5 minutes. After centrifugation, the supernatant (i.e., PBS) was discarded, pellets were crushed, and 10 ml of an IMDM culture solution (Gibco) containing 10% bovine fetal serum (MP Biomeicals) and a 1% Antibiotic/Antimycotic mixed solution (Nakarai) was added thereto. The resulting cell suspension was transferred to a 10-ml petri dish and allowed to stand still in the presence of 5% carbon dioxide at 37° C. in an incubator for 30 minutes so as to induce adhesion of monocytes. Then, the petri dish was washed 5 times with PBS and a culture solution was added again to adhering monocytes. Further, M-CSF (Pepro Tech) was added to result in a concentration of 25 ng/ml. The M-CSF-containing culture solution was replaced on Day 3 and Day 6. On Day 7, adhering cells (cells that had differentiated from monocytes into macrophages) were removed, and a culture solution was added to adjust the concentration to $1 \times 10^6$ cells/ml. This cell suspension (100 μl) was added to wells of a 96-well round-bottomed plate.

Meanwhile, a cell labeling kit (Sigma-Aldrich Co. LLC.) was used for PE labeling of KB cells (human oral-epidermoid-cancer-derived FRα-expressing cells). Briefly, 3.75 μl of a PE labeling reagent was added to 1 ml of PBS containing $1 \times 10^7$ KB cells for 1 minute. Then, a culture solution was added to adjust the concentration to $2 \times 10^5$ cells/ml. The resulting solution (100 μl was added to the above wells containing macrophages, and different antibodies were separately added to the wells to result in a concentration of 10 μg/ml. Experiments were run in triplicate.

The contents in the wells subjected to the same procedures were mixed 6 hours after culture and transferred to a Falcon tube, followed by staining for 30 minutes with the FITC-labeled anti-CD14 antibody (mouse $IgG_1$, South Biotech) and the FITC-labeled anti-CD11b antibody (mouse $IgG_1$, South Biotech) or with the FITC-labeled antibody (mouse $IgG_1$, South Biotech) for a negative control. Double staining analysis was conducted using a flow cytometer (CyAn, Beckman Coulter, Inc.).

FIG. 8 shows the analysis results. Panel A shows PE-labeled KB cells. Panel B shows macrophages that reacted with the FITC-labeled anti-CD14 antibody and the FITC-labeled anti-CD11b antibody. The presence of PE- and FITC-labeled cells means the occurrence of phagocytosis of KB cells by macrophages. Compared with the group supplemented with the control antibody (rat $IgG_{2a}$, South Biotech) (panel C), the group supplemented with antibody No. 5 (panel D) was found to have ADCP capacity (increase in the R9 region in the figure); however, the group supplemented with F (ab')$_2$ of antibody No. 5 (panel E) was found not to have ADCP capacity, indicating that ADCP capacity of antibody No. 5 (anti-human FRα/β rat monoclonal antibody) is exhibited depending on Fc receptors of macrophages. The results suggest that administration of the anti-human FRα/β rat monoclonal antibody results in promotion of phagocytosis of folate receptor α-expressing cancer cells by macrophages and inhibition of cancer cell growth.

EXAMPLE 6

Effects of Treating Cancer with Antibody Preparation Targeting FRα-Positive Human Cancer Cells and FRβ-Positive Mouse Infiltrating Macrophages IGROV-1 human cancer cells (ovarian-cancer-derived FRα-expressing cells) adjusted to $1 \times 10^7$ cells were peritoneally implanted into 9-12-week old NOD/SCID mice (female) (Day 0). On Day 4 after cancer cell implantation, 0.5 mL of 3% thioglycolate medium was peritoneally administered to induce mouse macrophages (FRβ-expressing macrophages). Further, antibodies adjusted to 100 μg were peritoneally administered on Days 8, 15, and 22. The date of death was tracked while the humanitarian endpoint was set at 45 days.

Figure 9:
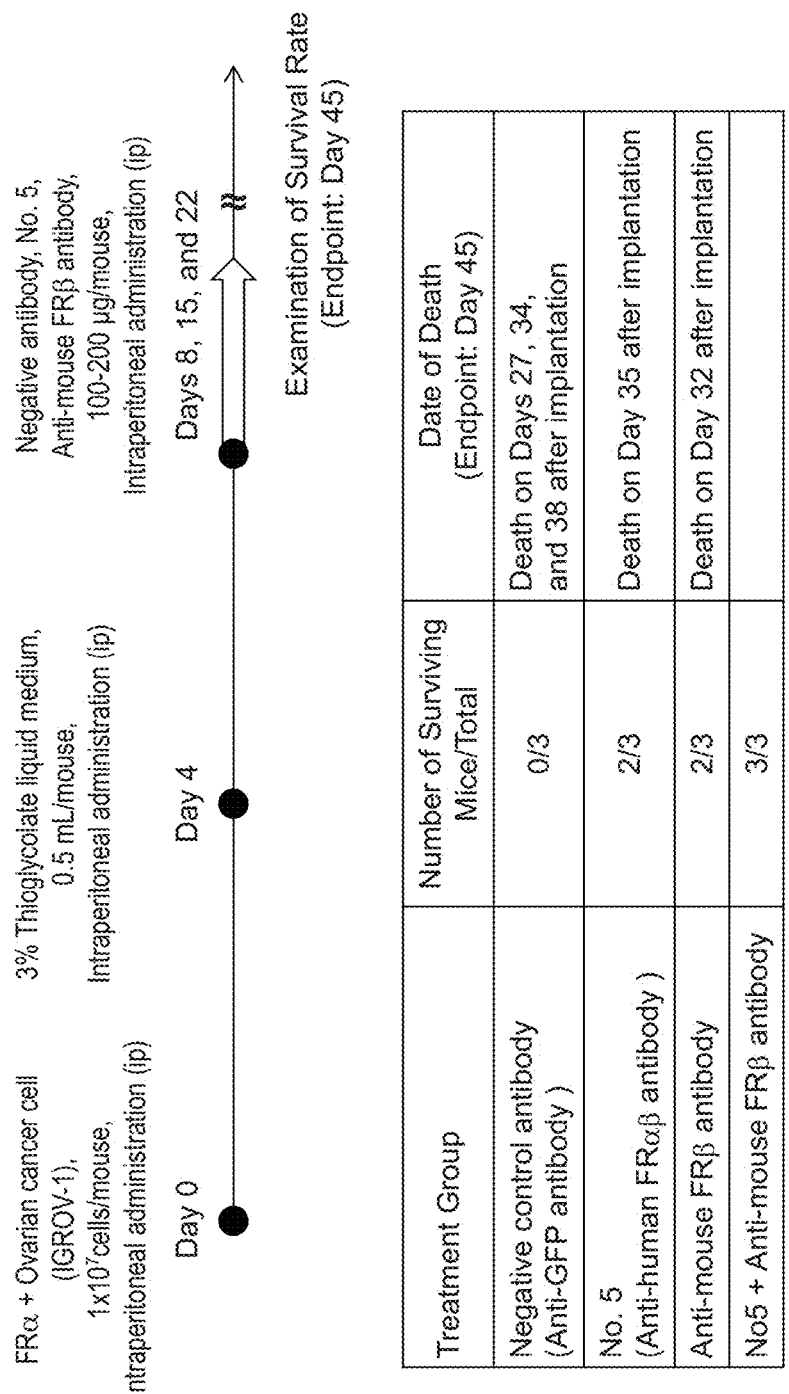
FIG. 9 shows an experimental schedule of cancer treatment with antibody preparations targeting FRα-positive human cancer cells and FRβ-positive mouse infiltrating macrophages and tracking results after cancer cell implantation.

FIG. 9 shows an experimental schedule and tracking results after cancer cell implantation. The survival rate of the negative control group was 0 while the survival rate was improved in the groups treated by monotherapy with antibody No. 5 (i.e., an anti-human FRα/β rat monoclonal antibody that reacts exclusively with human cancer cells but not with mouse macrophages in this experiment system) or the anti-mouse FRβ antibody. The survival rate at the endpoint reached 100% with the use of the combination therapy of both antibodies. The results suggest that removal of FRα-expressing cancer cells and FRβ-expressing macrophages is effective for treatment of ovarian cancer.

INDUSTRIAL APPLICABILITY

With the use of the molecular-targeted anticancer agent according to the present invention, cancer can be effectively treated by simultaneously damaging FRα-expressing cancer cells and cancer-related FRβ-expressing macrophages capable of promoting cancer growth. In addition, localization of various forms of cancer, the degree of malignancy, and therapeutic effects of cancer treatment can be assessed using the anti-FRα/β antibody or cancer diagnostic agent of the present invention.

All publications, patents, and patent applications cited herein are incorporated herein by reference in their entirety.

The invention claimed is:

1. An antibody, or a fragment thereof, capable of immunologically and specifically binding to a folate receptor α and a folate receptor β, in which the amino acid sequences of CDRH1, CDRH2, and CDRH3 of a heavy chain variable region (VH) are the amino acid sequences of SEQ ID NOs: 2, 4, and 6, respectively, and the amino acid sequences of CDRL1, CDRL2, and CDRL3 of a light chain variable region (VL) are the amino acid sequences of SEQ ID NOs: 10, 12, and 14, respectively.

2. The antibody according to claim 1, wherein the antibody is selected from the group consisting of a monoclonal antibody, a polyclonal antibody, a chimeric antibody, a single chain antibody, and a multispecific antibody.

3. The antibody according to claim 1, which is a human antibody or a humanized antibody.

4. A molecular-targeted anticancer agent, comprising a drug bound to the antibody of claim 1.

5. The molecular-targeted anticancer agent according to claim 4, wherein the drug is selected from the group consisting of a toxin, a cytotoxic agent, an enzyme, a cytokine, and a chemotherapeutic agent.

6. The molecular-targeted anticancer agent according to claim 5, wherein the toxin is a bacterium-derived toxin.

7. The molecular-targeted anticancer agent according to claim 6, wherein the bacterium-derived toxin is *Pseudomonas* toxin, *diphtheria* toxin, or staphylococcal toxin.

8. The molecular-targeted anticancer agent according to claim 5, wherein the cytotoxic agent is selected from the group consisting of an antitumor agent, a tumor growth inhibitor, a tumor cell apoptosis inducer, and a radioactive nuclide.

9. The molecular-targeted anticancer agent according to claim 4, wherein the molecular-targeted anticancer agent is an immunotoxin.

10. A pharmaceutical composition for cancer treatment, which comprises the molecular-targeted anticancer agent according to claim 4, and a pharmaceutically acceptable carrier.

11. A cancer diagnostic agent, which is obtained by binding a label to the antibody according to claim 1.

12. The cancer diagnostic agent according to claim 11, wherein the label is a fluorophore, a pigment, or a radioactive isotope.

13. The antibody of claim 1, that is selected from the group consisting of a monoclonal antibody, a polyclonal antibody, a chimeric antibody, and a multispecific antibody.

14. The antibody of claim 1, that is a monoclonal antibody.

15. An antibody capable of immunologically and specifically binding to a folate receptor α and a folate receptor β, in which the amino acid sequences of CDRH1, CDRH2, and CDRH3 of a heavy chain variable region (VH) are the amino acid sequences of SEQ ID NOs: 2, 4, and 6, respectively, and the amino acid sequences of CDRL1, CDRL2, and CDRL3 of a light chain variable region (VL) are the amino acid sequences of SEQ ID NOs: 10, 12, and 14, respectively.

* * * * *

```
                        SEQUENCE LISTING

<160> NUMBER OF SEQ ID NOS: 29

<210> SEQ ID NO 1
<211> LENGTH: 15
<212> TYPE: DNA
<213> ORGANISM: Rattus norvegicus
<220> FEATURE:
<221> NAME/KEY: CDS
<222> LOCATION: (1)..(15)

<400> SEQUENCE: 1 agc aat agt gta agc                                           15
Ser Asn Ser Val Ser
1               5

<210> SEQ ID NO 2
<211> LENGTH: 5
<212> TYPE: PRT
<213> ORGANISM: Rattus norvegicus

<400> SEQUENCE: 2

Ser Asn Ser Val Ser
1               5

<210> SEQ ID NO 3
<211> LENGTH: 48
<212> TYPE: DNA
<213> ORGANISM: Rattus norvegicus
<220> FEATURE:
<221> NAME/KEY: CDS
<222> LOCATION: (1)..(48)

<400> SEQUENCE: 3 gca ata tgg agt ggt gga agc aca gat tat aat tca gct ctc aaa tcc     48
Ala Ile Trp Ser Gly Gly Ser Thr Asp Tyr Asn Ser Ala Leu Lys Ser
1               5                   10                  15

<210> SEQ ID NO 4
<211> LENGTH: 16
<212> TYPE: PRT
<213> ORGANISM: Rattus norvegicus

<400> SEQUENCE: 4
```

```
Ala Ile Trp Ser Gly Gly Ser Thr Asp Tyr Asn Ser Ala Leu Lys Ser
1               5                   10                  15
```

<210> SEQ ID NO 5
<211> LENGTH: 27
<212> TYPE: DNA
<213> ORGANISM: Rattus norvegicus
<220> FEATURE:
<221> NAME/KEY: CDS
<222> LOCATION: (1)..(27)

<400> SEQUENCE: 5

```
tac tac ggg tat acc tac ttt gct tac                                27
Tyr Tyr Gly Tyr Thr Tyr Phe Ala Tyr
1               5
```

<210> SEQ ID NO 6
<211> LENGTH: 9
<212> TYPE: PRT
<213> ORGANISM: Rattus norvegicus

<400> SEQUENCE: 6

```
Tyr Tyr Gly Tyr Thr Tyr Phe Ala Tyr
1               5
```

<210> SEQ ID NO 7
<211> LENGTH: 351
<212> TYPE: DNA
<213> ORGANISM: Rattus norvegicus
<220> FEATURE:
<221> NAME/KEY: CDS
<222> LOCATION: (1)..(351)

<400> SEQUENCE: 7

```
cag gtg cag ctg aag gag tca gga cct ggt ctg gtg cag ccc tca cag    48
Gln Val Gln Leu Lys Glu Ser Gly Pro Gly Leu Val Gln Pro Ser Gln
1               5                   10                  15 acc ctg tcc ctc acc tgc act gtc tct ggg ttc tca tta acc agc aat    96
Thr Leu Ser Leu Thr Cys Thr Val Ser Gly Phe Ser Leu Thr Ser Asn
            20                  25                  30 agt gta agc tgg gtt cgc cag cct ccg gga aag ggt ctg gag tgg atg   144
Ser Val Ser Trp Val Arg Gln Pro Pro Gly Lys Gly Leu Glu Trp Met
        35                  40                  45 gga gca ata tgg agt ggt gga agc aca gat tat aat tca gct ctc aaa   192
Gly Ala Ile Trp Ser Gly Gly Ser Thr Asp Tyr Asn Ser Ala Leu Lys
    50                  55                  60 tcc cga ctg agc atc agt aag gac acc tcc aag agc caa gtt ttc tta   240
Ser Arg Leu Ser Ile Ser Lys Asp Thr Ser Lys Ser Gln Val Phe Leu
65                  70                  75                  80 aaa atg aac agt ctg caa act gaa gac aca gcc att tac ttc tgt acc   288
Lys Met Asn Ser Leu Gln Thr Glu Asp Thr Ala Ile Tyr Phe Cys Thr
                85                  90                  95 cga tac tac ggg tat acc tac ttt gct tac tgg ggc caa gga gtc atg   336
Arg Tyr Tyr Gly Tyr Thr Tyr Phe Ala Tyr Trp Gly Gln Gly Val Met
            100                 105                 110 gtc aca gtc tcc tca                                                351
Val Thr Val Ser Ser
        115
```

<210> SEQ ID NO 8
<211> LENGTH: 117
<212> TYPE: PRT
<213> ORGANISM: Rattus norvegicus

<400> SEQUENCE: 8

```
Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
            20                  25                  30

Ser Val Ser Trp Val Arg Gln Pro Pro Gly Lys Gly Leu Glu Trp Met
        35                  40                  45

Gly Ala Ile Trp Ser Gly Gly Ser Thr Asp Tyr Asn Ser Ala Leu Lys
    50                  55                  60

Ser Arg Leu Ser Ile Ser Lys Asp Thr Ser Lys Ser Gln Val Phe Leu
65                  70                  75                  80

Lys Met Asn Ser Leu Gln Thr Glu Asp Thr Ala Ile Tyr Phe Cys Thr
                85                  90                  95

Arg Tyr Tyr Gly Tyr Thr Tyr Phe Ala Tyr Trp Gly Gln Gly Val Met
            100                 105                 110

Val Thr Val Ser Ser
        115

<210> SEQ ID NO 9
<211> LENGTH: 33
<212> TYPE: DNA
<213> ORGANISM: Rattus norvegicus
<220> FEATURE:
<221> NAME/KEY: CDS
<222> LOCATION: (1)..(33)

<400> SEQUENCE: 9 cag gca agc caa gac att ggt aat tgg ttg gca                     33
Gln Ala Ser Gln Asp Ile Gly Asn Trp Leu Ala
1               5                   10

<210> SEQ ID NO 10
<211> LENGTH: 11
<212> TYPE: PRT
<213> ORGANISM: Rattus norvegicus

<400> SEQUENCE: 10

Gln Ala Ser Gln Asp Ile Gly Asn Trp Leu Ala
1               5                   10

<210> SEQ ID NO 11
<211> LENGTH: 21
<212> TYPE: DNA
<213> ORGANISM: Rattus norvegicus
<220> FEATURE:
<221> NAME/KEY: CDS
<222> LOCATION: (1)..(21)

<400> SEQUENCE: 11 gat gca atc aga ttg gca gat                                     21
Asp Ala Ile Arg Leu Ala Asp
1               5

<210> SEQ ID NO 12
<211> LENGTH: 7
<212> TYPE: PRT
<213> ORGANISM: Rattus norvegicus

<400> SEQUENCE: 12

Asp Ala Ile Arg Leu Ala Asp
1               5

<210> SEQ ID NO 13
```

-continued

```
<211> LENGTH: 45
<212> TYPE: DNA
<213> ORGANISM: Rattus norvegicus
<220> FEATURE:
<221> NAME/KEY: CDS
<222> LOCATION: (1)..(45)

<400> SEQUENCE: 13 att gga gac tat tac tgt caa cag ggt caa agt aat cct cgg acg      45
Ile Gly Asp Tyr Tyr Cys Gln Gln Gly Gln Ser Asn Pro Arg Thr
1               5                   10                  15

<210> SEQ ID NO 14
<211> LENGTH: 15
<212> TYPE: PRT
<213> ORGANISM: Rattus norvegicus

<400> SEQUENCE: 14

Ile Gly Asp Tyr Tyr Cys Gln Gln Gly Gln Ser Asn Pro Arg Thr
1               5                   10                  15

<210> SEQ ID NO 15
<211> LENGTH: 321
<212> TYPE: DNA
<213> ORGANISM: Rattus norvegicus
<220> FEATURE:
<221> NAME/KEY: CDS
<222> LOCATION: (1)..(321)

<400> SEQUENCE: 15 gac atc cag atg aca cag tct cct gcc tcc ctg tct gca tct ctg gaa      48
Asp Ile Gln Met Thr Gln Ser Pro Ala Ser Leu Ser Ala Ser Leu Glu
1               5                   10                  15 gaa att gtc acc atc aca tgc cag gca agc caa gac att ggt aat tgg      96
Glu Ile Val Thr Ile Thr Cys Gln Ala Ser Gln Asp Ile Gly Asn Trp
            20                  25                  30 ttg gca tgg tat cag cag aaa ccg ggg aaa tct cct cag ctc ctg att     144
Leu Ala Trp Tyr Gln Gln Lys Pro Gly Lys Ser Pro Gln Leu Leu Ile
        35                  40                  45 tat gat gca atc aga ttg gca gat ggg gtc cca tca cgg ttc agc ggc     192
Tyr Asp Ala Ile Arg Leu Ala Asp Gly Val Pro Ser Arg Phe Ser Gly
    50                  55                  60 agt aga tct ggc aca cag tat tct ctt aag atc agc aga cta cag gtt     240
Ser Arg Ser Gly Thr Gln Tyr Ser Leu Lys Ile Ser Arg Leu Gln Val
65                  70                  75                  80 gaa gat att gga gac tat tac tgt caa cag ggt caa agt aat cct cgg     288
Glu Asp Ile Gly Asp Tyr Tyr Cys Gln Gln Gly Gln Ser Asn Pro Arg
                85                  90                  95 acg ttc ggt gga ggc acc aag ctg gaa ttg aaa                         321
Thr Phe Gly Gly Gly Thr Lys Leu Glu Leu Lys
            100                 105

<210> SEQ ID NO 16
<211> LENGTH: 107
<212> TYPE: PRT
<213> ORGANISM: Rattus norvegicus

<400> SEQUENCE: 16

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro Gln Leu Leu Ile
        35                  40                  45
```

```
Tyr Asp Ala Ile Arg Leu Ala Asp Gly Val Pro Ser Arg Phe Ser Gly
         50                  55                  60

Ser Arg Ser Gly Thr Gln Tyr Ser Leu Lys Ile Ser Arg Leu Gln Val
 65                  70                  75                  80

Glu Asp Ile Gly Asp Tyr Tyr Cys Gln Gln Gly Gln Ser Asn Pro Arg
                 85                  90                  95

Thr Phe Gly Gly Gly Thr Lys Leu Glu Leu Lys
            100                 105

<210> SEQ ID NO 17
<211> LENGTH: 366
<212> TYPE: DNA
<213> ORGANISM: Artificial
<220> FEATURE:
<223> OTHER INFORMATION: synthetic
<220> FEATURE:
<221> NAME/KEY: CDS
<222> LOCATION: (7)..(357)

<400> SEQUENCE: 17 catatg cag gtg cag ctg aag gag tca gga cct ggt ctg gtg cag ccc      48
       Gln Val Gln Leu Lys Glu Ser Gly Pro Gly Leu Val Gln Pro
        1               5                   10 tca cag acc ctg tcc ctc acc tgc act gtc tct ggg ttc tca tta acc     96
Ser Gln Thr Leu Ser Leu Thr Cys Thr Val Ser Gly Phe Ser Leu Thr
 15                  20                  25                  30 agc aat agt gta agc tgg gtt cgc cag cct ccg gga aag tgt ctg gag    144
Ser Asn Ser Val Ser Trp Val Arg Gln Pro Pro Gly Lys Cys Leu Glu
                 35                  40                  45 tgg atg gga gca ata tgg agt ggt gga agc aca gat tat aat tca gct   192
Trp Met Gly Ala Ile Trp Ser Gly Gly Ser Thr Asp Tyr Asn Ser Ala
             50                  55                  60 ctc aaa tcc cga ctg agc atc agt aag gac acc tcc aag agc caa gtt   240
Leu Lys Ser Arg Leu Ser Ile Ser Lys Asp Thr Ser Lys Ser Gln Val
         65                  70                  75 ttc tta aaa atg aac agt ctg caa act gaa gac aca gcc att tac ttc   288
Phe Leu Lys Met Asn Ser Leu Gln Thr Glu Asp Thr Ala Ile Tyr Phe
 80                  85                  90 tgt acc cga tac tac ggg tat acc tac ttt gct tac tgg ggc caa gga   336
Cys Thr Arg Tyr Tyr Gly Tyr Thr Tyr Phe Ala Tyr Trp Gly Gln Gly
 95                 100                 105                 110 gtc atg gtc aca gtc tcc tca aaagcttcc                             366
Val Met Val Thr Val Ser Ser
                115

<210> SEQ ID NO 18
<211> LENGTH: 117
<212> TYPE: PRT
<213> ORGANISM: Artificial
<220> FEATURE:
<223> OTHER INFORMATION: Synthetic Construct

<400> SEQUENCE: 18

Gln Val Gln Leu Lys Glu Ser Gly Pro Gly Leu Val Gln Pro Ser Gln
 1               5                  10                  15

Thr Leu Ser Leu Thr Cys Thr Val Ser Gly Phe Ser Leu Thr Ser Asn
             20                  25                  30

Ser Val Ser Trp Val Arg Gln Pro Pro Gly Lys Cys Leu Glu Trp Met
         35                  40                  45

Gly Ala Ile Trp Ser Gly Gly Ser Thr Asp Tyr Asn Ser Ala Leu Lys
     50                  55                  60
```

```
Ser Arg Leu Ser Ile Ser Lys Asp Thr Ser Lys Ser Gln Val Phe Leu
 65                  70                  75                  80

Lys Met Asn Ser Leu Gln Thr Glu Asp Thr Ala Ile Tyr Phe Cys Thr
                 85                  90                  95

Arg Tyr Tyr Gly Tyr Thr Tyr Phe Ala Tyr Trp Gly Gln Gly Val Met
            100                 105                 110

Val Thr Val Ser Ser
        115

<210> SEQ ID NO 19
<211> LENGTH: 336
<212> TYPE: DNA
<213> ORGANISM: Artificial
<220> FEATURE:
<223> OTHER INFORMATION: synthetic
<220> FEATURE:
<221> NAME/KEY: CDS
<222> LOCATION: (7)..(327)

<400> SEQUENCE: 19 catatg gac atc cag atg aca cag tct cct gcc tcc ctg tct gca tct        48
       Asp Ile Gln Met Thr Gln Ser Pro Ala Ser Leu Ser Ala Ser
        1               5                   10 ctg gaa gaa att gtc acc atc aca tgc cag gca agc caa gac att ggt        96
Leu Glu Glu Ile Val Thr Ile Thr Cys Gln Ala Ser Gln Asp Ile Gly
 15                  20                  25                  30 aat tgg ttg gca tgg tat cag cag aaa ccg ggg aaa tct cct cag ctc       144
Asn Trp Leu Ala Trp Tyr Gln Gln Lys Pro Gly Lys Ser Pro Gln Leu
                 35                  40                  45 ctg att tat gat gca atc aga ttg gca gat ggg gtc cca tca cgg ttc       192
Leu Ile Tyr Asp Ala Ile Arg Leu Ala Asp Gly Val Pro Ser Arg Phe
             50                  55                  60 agc ggc agt aga tct ggc aca cag tat tct ctt aag atc agc aga cta       240
Ser Gly Ser Arg Ser Gly Thr Gln Tyr Ser Leu Lys Ile Ser Arg Leu
         65                  70                  75 cag gtt gaa gat att gga gac tat tac tgt caa cag ggt caa agt aat       288
Gln Val Glu Asp Ile Gly Asp Tyr Tyr Cys Gln Gln Gly Gln Ser Asn
 80                  85                  90 cct cgg acg ttc ggt tgt ggc acc aag ctg gaa ttg aaa taggaattc         336
Pro Arg Thr Phe Gly Cys Gly Thr Lys Leu Glu Leu Lys
 95                 100                 105

<210> SEQ ID NO 20
<211> LENGTH: 107
<212> TYPE: PRT
<213> ORGANISM: Artificial
<220> FEATURE:
<223> OTHER INFORMATION: Synthetic Construct

<400> SEQUENCE: 20

Asp Ile Gln Met Thr Gln Ser Pro Ala Ser Leu Ser Ala Ser Leu Glu
 1               5                   10                  15

Glu Ile Val Thr Ile Thr Cys Gln Ala Ser Gln Asp Ile Gly Asn Trp
             20                  25                  30

Leu Ala Trp Tyr Gln Gln Lys Pro Gly Lys Ser Pro Gln Leu Leu Ile
         35                  40                  45

Tyr Asp Ala Ile Arg Leu Ala Asp Gly Val Pro Ser Arg Phe Ser Gly
     50                  55                  60

Ser Arg Ser Gly Thr Gln Tyr Ser Leu Lys Ile Ser Arg Leu Gln Val
 65                  70                  75                  80
```

Glu Asp Ile Gly Asp Tyr Tyr Cys Gln Gln Gly Gln Ser Asn Pro Arg
            85                  90                  95

Thr Phe Gly Cys Gly Thr Lys Leu Glu Leu Lys
            100                 105

<210> SEQ ID NO 21
<211> LENGTH: 27
<212> TYPE: DNA
<213> ORGANISM: Artificial
<220> FEATURE:
<223> OTHER INFORMATION: primer

<400> SEQUENCE: 21
agaaagacat gggtctggaa atggatg                                      27

<210> SEQ ID NO 22
<211> LENGTH: 34
<212> TYPE: DNA
<213> ORGANISM: Artificial
<220> FEATURE:
<223> OTHER INFORMATION: primer

<400> SEQUENCE: 22
catatggact gaactcagcc aaggagccag agtt                              34

<210> SEQ ID NO 23
<211> LENGTH: 21
<212> TYPE: DNA
<213> ORGANISM: Artificial
<220> FEATURE:
<223> OTHER INFORMATION: primer

<400> SEQUENCE: 23
caccatggag ttactttga g                                             21

<210> SEQ ID NO 24
<211> LENGTH: 29
<212> TYPE: DNA
<213> ORGANISM: Artificial
<220> FEATURE:
<223> OTHER INFORMATION: primer

<400> SEQUENCE: 24
agcctccggg aaagtgtctg gagtggatg                                    29

<210> SEQ ID NO 25
<211> LENGTH: 29
<212> TYPE: DNA
<213> ORGANISM: Artificial
<220> FEATURE:
<223> OTHER INFORMATION: primer

<400> SEQUENCE: 25
catccactcc agacactttc ccggaggct                                    29

<210> SEQ ID NO 26
<211> LENGTH: 24
<212> TYPE: DNA
<213> ORGANISM: Artificial
<220> FEATURE:
<223> OTHER INFORMATION: primer

<400> SEQUENCE: 26
catatgcagg tgcagctgaa ggag                                         24

```
<210> SEQ ID NO 27
<211> LENGTH: 29
<212> TYPE: DNA
<213> ORGANISM: Artificial
<220> FEATURE:
<223> OTHER INFORMATION: primer

<400> SEQUENCE: 27
ggaagctttt gaggagactg tgaccatga                                29

<210> SEQ ID NO 28
<211> LENGTH: 27
<212> TYPE: DNA
<213> ORGANISM: Artificial
<220> FEATURE:
<223> OTHER INFORMATION: primer

<400> SEQUENCE: 28
catatggaca tccagatgac acagtct                                  27

<210> SEQ ID NO 29
<211> LENGTH: 42
<212> TYPE: DNA
<213> ORGANISM: Artificial
<220> FEATURE:
<223> OTHER INFORMATION: primer

<400> SEQUENCE: 29
gaattcctat ttcaattcca gcttggtgcc acaaccgaac gt                 42
```